(12) United States Patent
Grogan et al.

(10) Patent No.: US 9,651,555 B2
(45) Date of Patent: May 16, 2017

(54) METHOD OF IDENTIFYING TREATMENT RESPONSIVE NON-SMALL CELL LUNG CANCER USING ANAPLASTIC LYMPHOMA KINASE (ALK) AS A MARKER

(71) Applicant: Ventana Medical Systems, Inc., Tucson, AZ (US)

(72) Inventors: Thomas Grogan, Tucson, AZ (US); Michael Barnes, San Francisco, CA (US); June Clements, Tucson, AZ (US); Hiro Nitta, Tucson, AZ (US); Esteban Roberts, Tucson, AZ (US); Crystal Schemp, Tucson, AZ (US); Shalini Singh, Tucson, AZ (US); Penny Towne, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 14/430,532

(22) PCT Filed: Mar. 14, 2013

(86) PCT No.: PCT/US2013/031531
§ 371 (c)(1),
(2) Date: Mar. 23, 2015

(87) PCT Pub. No.: WO2014/046730
PCT Pub. Date: Mar. 27, 2014

(65) Prior Publication Data
US 2015/0346206 A1 Dec. 3, 2015

Related U.S. Application Data

(60) Provisional application No. 61/704,960, filed on Sep. 24, 2012.

(51) Int. Cl.
*G01N 33/574* (2006.01)
*A61K 31/4545* (2006.01)

(52) U.S. Cl.
CPC ... *G01N 33/57423* (2013.01); *A61K 31/4545* (2013.01); *G01N 2333/912* (2013.01); *G01N 2800/52* (2013.01)

(58) Field of Classification Search
None
See application file for complete search history.

(56) References Cited

U.S. PATENT DOCUMENTS

| 4,444,487 | A | 4/1984 | Miller et al. |
|---|---|---|---|
| 4,745,055 | A | 5/1988 | Schenk et al. |
| 7,230,098 | B2 | 6/2007 | Cui et al. |
| 7,585,643 | B2 | 9/2009 | Sem |
| 7,825,137 | B2 | 11/2010 | Christensen et al. |
| 8,217,057 | B2 | 7/2012 | Cui et al. |
| 2012/0171668 | A1 | 7/2012 | May et al. |

FOREIGN PATENT DOCUMENTS

| EP | 120694 A2 | 3/1984 |
|---|---|---|
| EP | 125023 A1 | 4/1984 |
| EP | 256654 A2 | 7/1987 |
| WO | 8803565 A1 | 5/1988 |
| WO | 2012070730 A1 | 5/2012 |

OTHER PUBLICATIONS

Yi et al. (J. Thorac. Oncol., 6:459-465, 2011).*
Soda et al., Nature 448:561-566, 2007.
Falkner et al., Nature 298:286, 1982.
Morrison, J. Immunol. 123:793, 1979.
Morrison et al., Ann Rev. Immunol. 2:239, 1984.
2004 World Health Organization classification of lung tumors, Beasley et al., Semin. Roentgenol. 40:90-97, 2004.
Kwak et al., N. Engl. J. Med. 363:1693-1703, 2010.
Shaw et al., Lancet Oncol. 12:1004-1012, 2011.
Yi et al., J. Thorac. Oncol. 6:459-465, 2011.
Mino-Kenudson et al., Clin. Cancer Res. 16:1561-1571, 2010.
Iwahara et al., Oncogene 14:439-449, 1997.
Thunnissen, et, al., Virchows Arch 461:245-257, 2012.
Peled, et, al., J. Thorac. Oncol. 7:14-16, 2012.
Nitta, et, al. J. Thorac. Oncol. 8:1019-1031, 2013.
International Application No. PCT/US2013/031531, International Search Report mailed Jun. 6, 2013.
International Application No. PCT/US2013/031531, Written Opinion mailed Jun. 6, 2013.
Chinese Office Action mailed Aug. 3, 2016 in corresponding CN Application No. 201380046571.2.
EPC Rule 114(2) Communication—Notification of a Third Party Observation mailed Oct. 27, 2016 in connection with corresponding EP Application No. 13712120.8.
Japanese Notice of Observation mailed Aug. 30, 2016 and Translation in corresponding JP Application No. 2015-533040.
Media Release, Ventana to collaborate with Pfizer and CST on companion diagnostic to identify lung cancer patients mith ALK gene re arrangements, Jan. 10, 2012, http://www.ventana.com/documents/media/Ventana_CST_Pfizer_Release.pdf, published: Jan. 10, 2012.
OptiView Detection Chemistry, http://www.ventana.com/documents/OptiView_F&B_Brochure.pdf, published 2011.

(Continued)

*Primary Examiner* — Brad Duffy
*Assistant Examiner* — Nelson B Moseley, II
(74) *Attorney, Agent, or Firm* — Ventana Medical Systems, Inc.

(57) ABSTRACT

Disclosed herein are methods for identifying a subject as having NSCLC that is predicted or is likely to respond to treatment with an ALK inhibitor, for example crizotinib. The methods include identifying a sample including NSCLC tumor cells as ALK-positive or ALK-negative using immunohistochemistry (IBC) and scoring methods disclosed herein. A subject is identified as having NSCLC likely to respond to treatment with an ALK inhibitor if the sample is identified as ALK-positive and is identified as having NSCLC not likely to respond to treatment with an ALK inhibitor if the sample is identified as ALK-negative. According to certain embodiments of the methods, subjects predicted to respond to an ALK inhibitor may then be treated with an ALK inhibitor such as crizotinib.

3 Claims, 22 Drawing Sheets
(22 of 22 Drawing Sheet(s) Filed in Color)

(56) References Cited

OTHER PUBLICATIONS

Takeuchi, K. et al., ALK-positive lung cancer—Diagnosis based on and pathologic tissue images of formalin-fixed paraffin-embedded samples, Journal of Clinical and Experimental Medicine, (2011), pp. 1105-1111, vol. 237 No. 12.

Eunhee S. Yi, MD et al., Correlation of IHC and FISH for ALK Gene Rearrangement in Non-Small Cell Lung Carcinoma, IHC Score Algorithm for FISH, Journal of Thoracic Oncology, 2011, vol. 6, No. 3, pp. 1-7.†

Ventana OptiView DAB IHC Detection Kit Product Sheet, Jun. 23, 2011, pp. 1-4.†

Mari Mino-Kenudson et al., A Novel, Highly Sensitive Antibody Allows for the Routine Detection of ALK-Rearranged Lung Adenocarcinomas by Standard Immunohistochemistry, Clinical Cancer Research, 2010, vol. 16, No. 5, pp. 1561-1571.†

FDA News Release, FDA approves Xalkori with companion diagnostic for a type of late-stage lung cancer, Aug. 26, 2011, pp. 1-3.†

Erik Thunnissen et al., EML4-ALK testing in non-small cell carcinomas of the lung; a review with recommendations, Virchows Arch, 2012, vol. 461, pp. 245-257.†

\* cited by examiner
† cited by third party

METHOD OF IDENTIFYING TREATMENT RESPONSIVE NON-SMALL CELL LUNG CANCER USING ANAPLASTIC LYMPHOMA KINASE (ALK) AS A MARKER

CROSS REFERENCE TO RELATED APPLICATION

This is a national stage entry of PCT/US2013/031531, filed Mar. 14, 2013, which claims the benefit of U.S. Provisional Application No. 61/704,960, filed Sep. 24, 2012, which are incorporated herein by reference in their entirety.

FIELD

This application relates to embodiments of a method for prognosing non-small cell lung carcinoma, particularly a method of determining whether a non-small lung carcinoma is predicted to respond to an anaplastic lymphoma kinase inhibitor.

BACKGROUND

Anaplastic lymphoma kinase (ALK) protein is a member of the insulin receptor superfamily of receptor tyrosine kinases. ALK is a type I membrane glycoprotein that is normally expressed only in the nervous system. An inversion within chromosome 2p, resulting in the formation of a fusion gene product comprising portions of the echinoderm microtubule associated protein-like 4 (EML4) gene and the ALK gene, was discovered in non-small cell lung carcinoma (NSCLC) cell lines and archived clinical specimens (Soda et al., Nature 448:561-566, 2007). ALK is now recognized as a critical player in NSCLC, and although EML4 is the predominant fusion partner, other fusion partner genes have been identified. The incidence of ALK gene rearrangements appears to range from 2-7%, translating to about 6,000 ALK positive patients/year in the United States and about 40,000 patients/year worldwide. Importantly, ALK gene rearrangements are rarely coincident with EGFR, HER2, or KRAS mutations, demonstrating that ALK positivity is a distinct disease subtype.

Crizotinib (XALKORI, Pfizer) is a potent receptor tyrosine kinase inhibitor that inhibits ALK. In two clinical trials, ALK-positive locally advanced or metastatic NSCLC patients who were treated with crizotinib exhibited overall response rates of 50% (N=136; 95% CI: 42%, 59%) and 61% (N=119; 95% CI: 52%, 70%), respectively. Thus, determination of ALK status in NSCLC patients is critical for directing patient care. However, there remains a need for a specific, sensitive, and standardized assay for ALK status to quickly and accurately identify NSCLC patients most likely to be responsive to crizotinib treatment.

SUMMARY

Disclosed herein are embodiments of a method for identifying a subject as having NSCLC that is predicted to respond to treatment with an ALK inhibitor, for example crizotinib. The embodiments include identifying a sample including NSCLC tumor cells as ALK-positive or ALK-negative using immunohistochemistry (IHC) and scoring methods disclosed herein. A subject is identified as having NSCLC likely to respond to treatment with an ALK inhibitor if the sample is identified as ALK-positive and is identified as having NSCLC not likely to respond to treatment with an ALK inhibitor if the sample is identified as ALK-negative.

In some examples, a sample is labeled with an anti-ALK antibody and the sample is identified as ALK-positive if at least one tumor cell with strong granular cytoplasmic staining is present in the sample.

Some embodiments of the disclosed method also include selecting a subject having an ALK-positive NSCLC tumor for treatment with an ALK inhibitor. Additional embodiments of the disclosed method also include treating a subject identified as having NSCLC that is predicted to response to treatment, such as by administering an ALK inhibitor (such as crizotinib) to a subject having an ALK-positive NSCLC tumor alone or in combination with other known or future developed treatments.

The foregoing and other features of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

I. Abbreviations

Figure 1A:
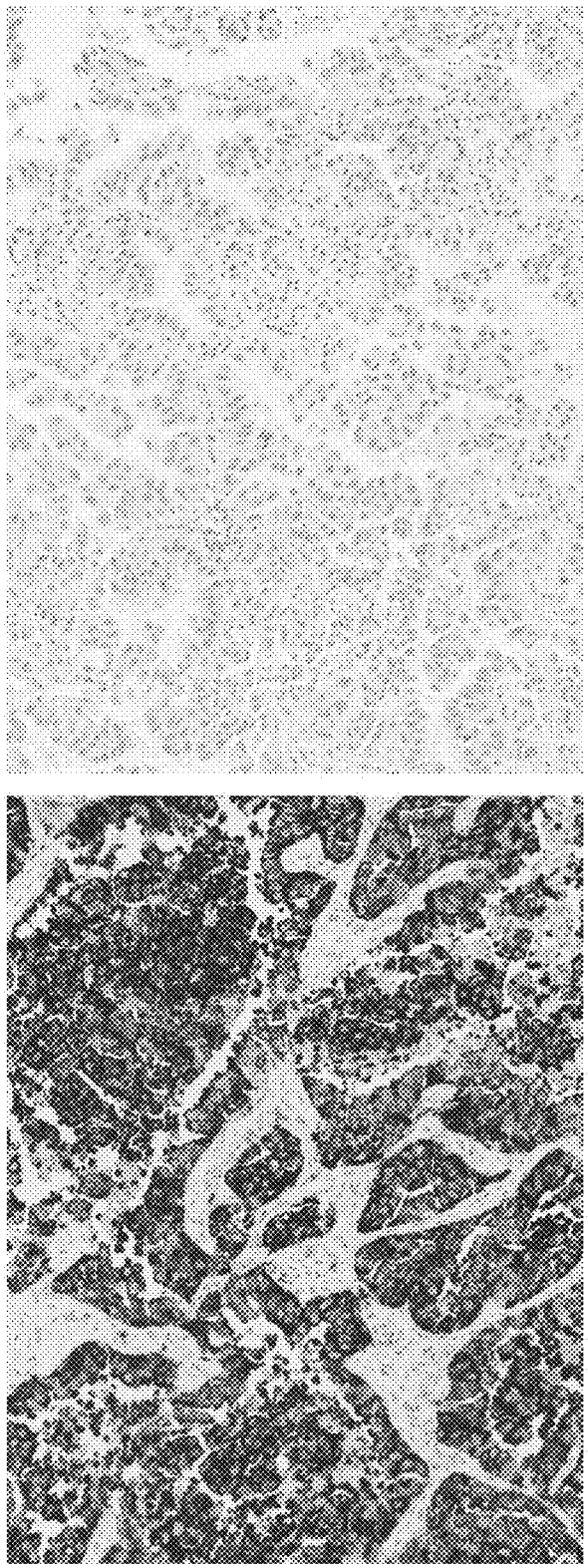
FIGS. 1A and 1B are digital images of two exemplary ALK-positive cases showing homogeneous ALK IHC expression on anti-ALK (D5F3) staining (left panels) and matched rabbit monoclonal negative control Ig staining (right panels).
Figure 1B:
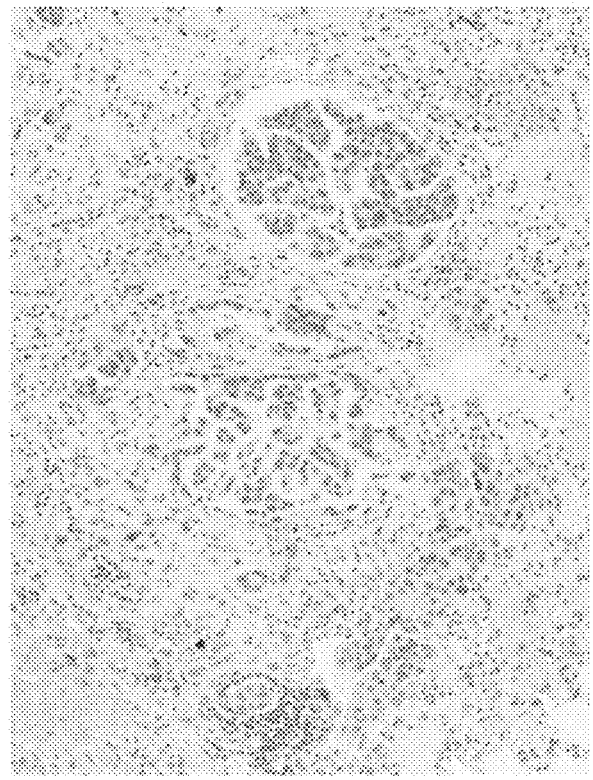
Figure 1B:
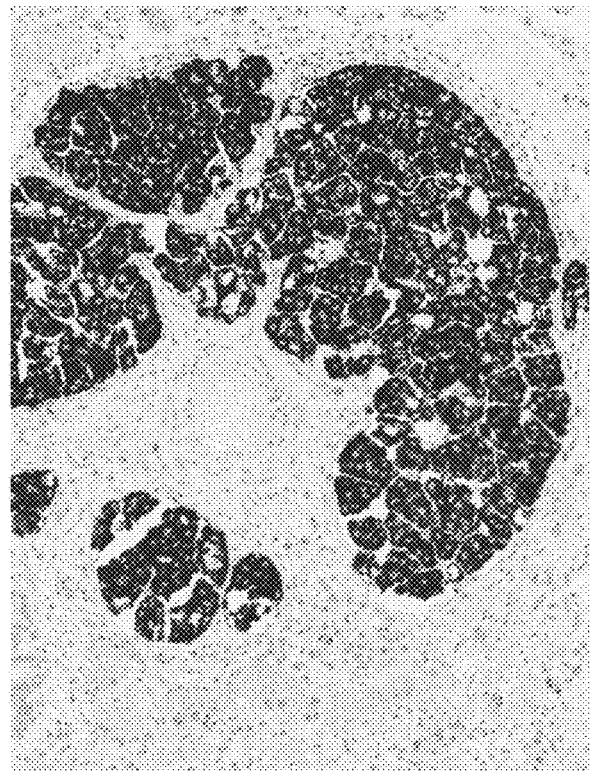

ALK anaplastic lymphoma kinase
DAB 3,3'-diaminobenzidine tetrahydrochloride
FISH fluorescent in situ hybridization
H&E hematoxylin & eosin
HQ 3-hydroxyquinoxaline-2-carboxylic acid
HRP horseradish peroxidase
IHC immunohistochemistry
NSCLC non-small cell lung carcinoma II. Terms The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising an antibody" includes single or plural antibodies and is considered equivalent to the phrase "comprising at least one antibody." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Dates of GenBank Accession Nos. referred to herein are the sequences available at least as early as Sep. 24, 2012.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

In order to facilitate review of the various embodiments of the disclosure, the following explanations of specific terms are provided:

Anaplastic lymphoma kinase (ALK): A member of the insulin receptor superfamily of receptor tyrosine kinases. ALK comprises an extracellular domain, a single pass transmembrane domain and an intracellular tyrosine kinase domain. Chromosomal rearrangements resulting in ALK fusion genes are found in several tumor types, including anaplastic large cell lymphoma, neuroblastoma, and non-small cell lung cancer. ALK/EML4 is the most common ALK gene fusion; additional ALK fusions include ALK/RANBP2, ALK/ATIC, ALK/TFG, ALK/NPM1, ALK/SQSTM1, ALK/KIF5B, ALK/CLTC, ALK/TPM4, and ALK/MSN.

ALK sequences are publically available, for example from GenBank® sequence database (e.g., accession numbers NP_004295 (protein), and NM_004304 (nucleic acid)). One of ordinary skill in the art can identify additional ALK nucleic acid and protein sequences, including ALK variants and/or ALK gene fusions.

An ALK inhibitor is a molecule that inhibits or decreases ALK activity, such as ALK tyrosine kinase activity. In some examples, an ALK inhibitor can be a small molecule, a protein (such as an antibody), or a nucleic acid (such as an antisense molecule). An ALK inhibitor may inhibit or decrease binding of a ligand (such as pleiotrophin) to ALK and thus decrease ALK tyrosine kinase activity. An ALK inhibitor may also directly inhibit or decrease ALK tyrosine kinase activity, for example, an ATP-competitive inhibitor (such as crizotinib). Molecules that decrease or inhibit expression of ALK, such as antisense molecules, are also ALK inhibitors. In some examples, ALK inhibitors inhibit or decrease activity of a genetically altered ALK, such as an ALK gene fusion (including, but not limited to ALK/EML4 gene fusions). The ALK inhibitor may specifically inhibit ALK tyrosine kinase activity or may inhibit other receptor tyrosine kinase activity (such as c-Met/HGFR activity), in addition to inhibiting ALK tyrosine kinase activity. Antibody: Immunoglobulin molecules and immunologically active portions of immunoglobulin molecules, that is, molecules that contain an antigen binding site that specifically binds (immunoreacts with) an antigen (such as ALK). Exemplary antibodies include monoclonal, polyclonal, and humanized antibodies.

A naturally occurring antibody (such as IgG, IgM, IgD) includes four polypeptide chains, two heavy (H) chains and two light (L) chains interconnected by disulfide bonds. As used herein, the term antibody also includes recombinant antibodies produced by expression of a nucleic acid that encodes one or more antibody chains in a cell (for example see U.S. Pat. No. 4,745,055; U.S. Pat. No. 4,444,487; WO 88/03565; EP 256,654; EP 120,694; EP 125,023; Faoulkner et al., *Nature* 298:286, 1982; Morrison, *J. Immunol.* 123: 793, 1979; Morrison et al., *Ann Rev. Immunol.* 2:239, 1984).

The term antibody also includes an antigen binding fragment of a naturally occurring or recombinant antibody. Specific, non-limiting examples of binding fragments encompassed within the term antibody include Fab, (Fab')$_2$, Fv, and single-chain Fv (scFv). Fab is the fragment that contains a monovalent antigen-binding fragment of an antibody molecule produced by digestion of whole antibody with the enzyme papain to yield an intact light chain and a portion of one heavy chain or equivalently by genetic engineering. Fab' is the fragment of an antibody molecule obtained by treating whole antibody with pepsin, followed by reduction, to yield an intact light chain and a portion of the heavy chain; two Fab' fragments are obtained per antibody molecule. (Fab')$_2$ is the fragment of the antibody obtained by treating whole antibody with the enzyme pepsin without subsequent reduction or equivalently by genetic engineering. F(Ab')$_2$ is a dimer of two FAb' fragments held together by disulfide bonds. Fv is a genetically engineered fragment containing the variable region of the light chain and the variable region of the heavy chain expressed as two chains. Single chain antibody ("SCA") is a genetically engineered molecule containing the variable region of the light chain, the variable region of the heavy chain, linked by a suitable polypeptide linker as a genetically fused single chain molecule. Methods of making these fragments are routine in the art.

Chromogen: A substance capable of conversion to a colored product, such as a pigment or dye. Certain chromogens are electron donors that, when oxidized become a colored product. Production of a colored product, and the property of becoming insoluble upon chemical conversion, such as by oxidation, make chromogens useful for IHC. Particular examples of chromogenic compounds, without limitation, include 3,3'-diaminobenzidine (DAB), 4-nitrophenylphospate (pNPP), Fast Red, Fast Blue, bromochloroindolyl phosphate (BCIP), nitro blue tetrazolium (NBT), BCIP/NBT, AP Orange, AP Blue, tetramethylbenzidine (TMB), 2,2'-azino-di-[3-ethylbenzothiazoline sulphonate] (ABTS), o-dianisidine, 4-chloronaphtol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), New Fuchsin, iodonitrotetrazolium (INT), tetrazolium blue and tetrazolium violet.

Contact: To bring one agent into close proximity to another agent, thereby permitting the agents to interact. For example, an antibody can be applied to a microscope slide or other surface containing a biological sample, thereby permitting detection of proteins in the sample that are specifically recognized by the antibody.

Crizotinib: A receptor tyrosine kinase inhibitor that potently inhibits ALK. Crizotinib (also known as PF-02341066 or XALKORI, Pfizer) is an orally available selective ATP-competitive small molecule inhibitor of ALK and c-Met/HGFR tyrosine kinases and their oncogenic variants. See, e.g., U.S. Pat. Nos. 7,230,098; 7,825,137; 7,858,643; and 8,217,057; each of which is incorporated herein by reference in its entirety. Crizotinib can be used to treat patients with ALK-positive NSCLC.

Detect: To determine if an agent is present or absent. In some examples this can further include quantification. For example, use of an antibody specific for a particular protein (e.g., ALK) permits detection of the protein in a sample, such as a sample containing NSCLC tissue. In particular examples, an emission signal from a detectable label (such as an increase in the signal if the target is present) is detected. Detection can be in bulk, so that a macroscopic number of molecules can be observed simultaneously. Detection can also include identification of signals from single molecules using microscopy and such techniques as total internal reflection to reduce background noise.

Label: An agent capable of detection, for example by spectrophotometry, flow cytometry, or microscopy (such as light microscopy). For example, one or more labels can be attached to an antibody, thereby permitting detection of the target protein. Exemplary labels include radioactive isotopes, fluorophores, ligands, chemiluminescent agents, haptens, enzymes, and combinations thereof.

Non-small cell lung carcinoma (NSCLC): Any type of lung cancer other than small cell lung cancer. NSCLC includes squamous cell carcinoma (SQCC), adenocarcinoma (ADC), and large cell carcinoma. Both ADC and large cell carcinoma are classified as non-squamous cell type carcinoma. ADC can be grouped into subclasses, including acinar carcinoma, papillary carcinoma, bronchoalveolar carcinoma (BAC), solid tumor, and mixed subtypes (2004 World Health Organization classification of lung tumors, Beasley et al., *Semin. Roentgenol.* 40:90-97, 2004). ADC accounts for about 40% of all lung cancers and is the most common form of lung cancer among individuals who have never smoked. ADC is classified as a non-squamous cell type of NSCLC. Histologically, ADC shows gland formation, papillary structures, or solid growth with mucin production. Large cell carcinoma includes the subclasses giant cell tumors, clear cell carcinoma, adenosquamous carcinoma, and undifferentiated carcinoma.

Normal cells or tissue: Non-tumor, non-malignant cells and tissue.

Sample: A biological specimen containing genomic DNA, RNA (including mRNA), protein, or combinations thereof, obtained from a subject. Examples include a specimen containing at least one NSCLC cell (an "NSCLC sample"), for example, a tissue or tumor biopsy, fine needle aspirate, bronchoalveolar lavage, pleural fluid, sputum, surgical specimen, lymph node, an NSCLC metastasis, peripheral blood, or autopsy material. In other examples, a sample includes a control sample, such as a non-NSCLC cell or tissue sample.

Sensitivity and specificity: Statistical measurements of the performance of a binary classification test. Sensitivity measures the proportion of actual positives which are correctly identified (e.g., the percentage of NSCLC tumors that are identified as being ALK-positive that are identified as ALK-positive by another method, such as FISH). Specificity measures the proportion of negatives which are correctly identified (e.g., the percentage of NSCLC tumors identified as ALK-negative that are identified as ALK-negative by another method, such as FISH).

Subject: Living multi-cellular vertebrate organisms, a category that includes human and non-human mammals, such as veterinary subjects. In a particular example, a subject is one who has or is suspected of having lung cancer, such as NSCLC.

Therapeutically effective amount: A dose sufficient to prevent advancement, delay progression, or to cause regression of a disease, or which is capable of reducing symptoms caused by the disease, such as cancer, for example lung carcinoma (such as NSCLC).

Under conditions sufficient for: A phrase that is used to describe any environment that permits the desired activity. An example includes contacting an antibody with a NSCLC sample sufficient to allow detection of one or more target molecules (e.g., ALK) in the sample.

III. Methods of Identifying a Subject as Having a Tumor Likely to Respond to ALK Inhibitors Disclosed herein are embodiments of a method for identifying a subject as having NSCLC that is predicted to respond to treatment with an ALK inhibitor, for example crizotinib. The embodiments include identifying an NSCLC tumor as ALK-positive or ALK-negative using immunohistochemistry (IHC) and scoring methods disclosed herein. A subject is identified as having NSCLC likely or predicted to respond to treatment with an ALK inhibitor if the NSCLC tumor is identified as being ALK-positive and is identified as having an NSCLC tumor not likely or not predicted to respond to treatment with an ALK inhibitor if the NSCLC tumor is identified as ALK-negative.

Current methods for selecting a subject with NSCLC for treatment with an ALK inhibitor are based on determining whether the subject's tumor is ALK-positive utilizing a fluorescent in situ hybridization (FISH) assay. However, FISH presents several disadvantages compared to the methods disclosed herein. FISH assays are more time consuming, more expensive, and require substantially more specialized expertise for interpretation of results than IHC methods, such as those disclosed herein. In addition, the methods disclosed herein provide a "binary" scoring method that identifies NSCLC tumors as ALK-positive or ALK-negative with high sensitivity and specificity.

Rapid and accurate identification of ALK-positive NSCLC (e.g., having an ALK gene rearrangement and/or expressing ALK in the tumor) is critical for guiding patient care. Subjects with ALK-positive NSCLC treated with an ALK inhibitor (crizotinib) exhibited overall response rates of greater than 50% (e.g., Kwak et al., *N. Engl. J. Med.* 363:1693-1703, 2010; Shaw et al., *Lancet Oncol.* 12:1004-1012, 2011). ALK gene rearrangement in NSCLC is estimated to have a prevalence of about 2-7%. Therefore, accurate identification of ALK-positive NSCLC is needed to select subjects most likely to benefit from ALK inhibitor therapy. However, the currently used FISH "break-apart" assay presents significant challenges in sample interpretation. For example, intra-chromosomal gene rearrangements may produce subtle, difficult to detect, signal splitting, which leads to potential false negative results. In addition, the FISH assay requires enumeration of signal pattern for 50 nuclei. If less than 5 cells out of 50 are positive, the sample is considered to be ALK-negative; if more than 25 cells out of 50 are positive the sample is considered to be ALK-positive. However, if 5-25 positive cells are present, the sample is equivocal and a second reader is required; then, if the average percent positive cells is >15%, the sample is considered to be ALK-positive. Thus, the FISH assay can produce a significant number of "equivocal" results, necessitating time consuming and costly additional testing. Furthermore, samples are not tested by FISH if they do not meet the minimum tumor content requirement of at least 50 cells, so in many cases specimens such as fine needle aspirates or FFPE cytology samples are never tested by FISH. Finally, FISH has a failure rate of about 10-30%, meaning that many specimens will never have an ALK result and ALK-positive subjects may be missed and not obtain optimal treatment.

In contrast, the disclosed embodiments utilize IHC detection of ALK. IHC methods are rapid, routine in anatomical pathology laboratories, utilize light microscopy (as compared to FISH, which requires specialized dark-field fluorescence microscopy), are less expensive than FISH, and do not require specialized expertise for interpretation. In addition, the disclosed embodiments can be automated, which provides standardized staining and further improves sensitivity and specificity of the assay. Another advantage of the disclosed IHC methods is that there is no pre-specified tumor cell content requirement (whereas the FISH assay requires at least 50 tumor cells). In addition, the disclosed IHC method enables the pathologist or reader to evaluate the entire tissue sample (in contrast to FISH methods). For FISH, only a portion of the sample identified as containing tumor is contacted with the FISH reagents. Therefore, if ALK is present in a different tumor area on the tissue, it will not be identified. In contrast, the disclosed method enables the reader to see the entire tumor on the slide, in the context of the entire tissue sample. Finally, the scoring methods disclosed herein are "binary" (positive or negative) and therefore provide unequivocal results. Even previous IHC methods for detecting ALK-positive NSCLC tumors produced frequent equivocal results requiring additional testing (e.g., Yi et al., *J. Thorac. Oncol.* 6:459-465, 2011) or utilized semiquantitative grading of staining intensity and estimation of percentage of immunoreactive tumor cells (e.g., Mino-Kenudson et al., *Clin. Cancer Res.* 16:1561-1571, 2010). However, the disclosed IHC and scoring methods provide sensitive and specific identification of an NSCLC tumor as ALK-positive even if only a few tumor cells (or even only one tumor cell) exhibit strong granular cytoplasmic staining with an ALK antibody.

A. Detection of ALK

In particular examples, a sample obtained from the subject is analyzed to determine if it contains ALK protein, such as detectable levels of ALK protein in one or more tumor cells. Thus, the sample can be analyzed to detect or measure the presence of ALK protein in the sample, for example a qualitative or semi-quantitative measurement. In particular examples, the disclosed methods utilize qualitative measurement of the presence of ALK protein in tumor cells in the sample.

The disclosed embodiments utilize IHC to detect ALK protein in a sample from the subject. IHC is a method of determining the presence or distribution of an antigen (such as a protein) in a sample (such as an NSCLC sample, for example, a portion or section of tissue including NSCLC tumor cells or tissue) by detecting interaction of the antigen with a specific binding agent, such as an antibody. A sample including an antigen (such as a target antigen) is incubated with an antibody under conditions permitting antibody-antigen binding. Antibody-antigen binding can be detected by means of a detectable label conjugated to the antibody (direct detection) or by means of a detectable label conjugated to a secondary antibody, which is raised against the primary antibody (e.g., indirect detection). In other examples of indirect detection, antibody-antigen binding is detected by means of a detectable label conjugated to a tertiary antibody which is capable of binding to a secondary antibody (e.g., is raised against the secondary antibody or is raised against a molecule conjugated to the secondary antibody, such as a hapten). Exemplary detectable labels that can be used for IHC include, but are not limited to, radioactive isotopes, fluorochromes (such as fluorescein, fluorescein isothiocyanate, and rhodamine), haptens, enzymes (such as horseradish peroxidase or alkaline phosphatase), and chromogens (such as 3,3'-diaminobenzidine (DAB) or Fast Red). In some examples, detection of antigen-antibody binding also includes signal amplification (such as tyramide signal amplification or related methods). The signal amplification method may include methods described in U.S. Pat. Publ. No. 2012/0171668, incorporated by reference herein in its entirety.

In some examples, the specific binding agent is an antibody, such as a polyclonal or monoclonal antibody, or fragment thereof. In some examples, the antibody is a humanized antibody. In some examples, the antibody is a chimeric antibody. If desired, the antibody can include a detectable label to permit detection and in some cases quantification of the target protein/antibody complex. In other examples, the antibody is detected with an appropriate labeled secondary antibody. In additional examples, the antibody is detected with an appropriate labeled tertiary antibody.

In some examples, the antibody for ALK is obtained from Ventana Medical Systems, Inc. (Tucson, Ariz.). In specific examples, the antibody is anti-ALK D5F3 rabbit monoclonal antibody (Ventana, Catalog No. 790-4794). However, a person of ordinary skill in the art will appreciate that other antibodies that can be used in the methods provided herein are commercially available from other sources, including, but not limited to anti-ALK 5A4 antibody (Abcam, Cambridge, Mass.; Santa Cruz Biotechnology, Santa Cruz, Calif.), anti-ALK ALK1 antibody (Dako, Carpinteria, Calif.), and anti-ALK D9E antibody (Cell Signaling Technology, Danvers, Mass.). One of ordinary skill in the art can select additional anti-ALK antibodies, including those now available or developed in the future, that can be used in the disclosed methods.

In some examples, a lung cancer sample (such as a sample including NSCLC tumor tissue) is obtained, and processed for IHC. For example, the sample can be fixed and embedded, for example with formalin and paraffin. The sample can then be mounted on a support, such as a glass microscope slide. For example, the sample can be sliced into a series of thin sections (for example, using a microtome), and the sections mounted onto a microscope slide. In some examples, a single slide includes multiple tissue sections from the same lung cancer sample or sections from the same lung cancer sample can be placed on different slides. Different sections of the lung cancer (e.g., NSCLC tumor) sample can then be individually labeled with different antibodies, for example an anti-ALK antibody and a negative control antibody (for example, an antibody that does not specifically bind to an endogenous antigen in the sample). That is, one section can be labeled with anti-ALK antibody and another section can be labeled with a negative control antibody (such as an antibody that binds to a target that does not occur endogenously in the sample). In some examples, the slide labeled with an anti-ALK antibody (or a negative control antibody) is also stained with hematoxylin and eosin (H&E) (for example, to provide morphological or histological information, such as to discriminate cell types in the sample). In other examples, a separate slide from the same subject is labeled with H&E (such as a serial section from the same NSCLC sample). In some examples, additional proteins of interest can be detected in the same or additional tissue samples by labeling with further antibodies (for example, anti-EGFR antibodies, anti-RAS antibodies, and/or anti-HER2 antibodies). In some examples, an automated slide stainer (such as BENCHMARK instruments from Ventana Medical Systems, for example BENCHMARK XT or BENCHMARK GX instruments) can be used to stain and process the slides.

In some examples, detecting ALK protein in the sample includes indirect detection of binding of the anti-ALK antibody to the sample (for example, the anti-ALK (primary) antibody is not detectably labeled). For example, the sample is contacted with the anti-ALK antibody (such as anti-ALK D5F3 antibody) under conditions sufficient for the anti-ALK antibody to bind to ALK protein in the sample. The sample is then contacted with a secondary antibody that can specifically bind to the anti-ALK antibody (such as an anti-rabbit antibody, if the anti-ALK antibody is a rabbit antibody) under conditions sufficient for the secondary antibody to bind to the anti-ALK antibody. The secondary antibody can be detectably labeled. The detectable label can be conjugated to the secondary antibody. In some examples, the detectable label conjugated to the secondary antibody can be directly detected (such as a fluorescent label, or an enzyme, which can produce a detectable reaction product in the presence of suitable substrate). In other examples, the secondary antibody is conjugated to one or more haptens (such as fluorescein, dinitrophenyl, biotin, or 3-hydroxyquinoxaline-2-carboxylic acid (HQ)). The sample is then contacted with a tertiary antibody that can specifically bind the hapten-conjugated secondary antibody (for example, an anti-hapten antibody, such as an anti-HQ antibody) under conditions sufficient for the tertiary antibody to bind to the hapten. In some examples, the tertiary antibody is conjugated to a detectable label, such as an enzyme (for example, horseradish peroxidase (HRP) or alkaline phosphatase (AP)). The sample is then contacted with one or more reagents that produce a detectable reaction product in the presence of the enzyme. In some examples, the sample is contacted with an HRP substrate (such as hydrogen peroxide) and a chromogen (such as DAB) that produces a visually detectable product in the presence of HRP. In some examples, detecting ALK protein in the sample is carried out using OPTIVIEW DAB IHC Detection Kit (Ventana Medical Systems, Inc., Tucson, Ariz., Catalog No. 760-700).

In further examples, detecting ALK protein in the sample includes indirect detection including signal amplification. In some examples, signal amplification allows unequivocal detection of ALK positive specimens which may exhibit only weak staining without signal amplification. Signal amplification methods for IHC are known to one of ordinary skill in the art. In some examples, signal amplification includes CAtalyzed Reporter Deposition (CARD), also known as Tyramide Signal Amplification (TSA™). In one variation of this method an enzyme-conjugated secondary antibody (such as an HRP-conjugated secondary antibody) binds to the primary antibody. Next a substrate of biotinylated tyramide (tyramine is 4-(2-aminoethyl)phenol) is used, which presumably becomes a free radical when interacting with the HRP enzyme. The phenolic radical then reacts quickly with the surrounding material, thus depositing or fixing biotin in the vicinity. This process is repeated by providing more substrate (biotinylated tyramide) and building up more localized biotin. Finally, the "amplified" biotin deposit is detected with streptavidin attached to a fluorescent molecule. Alternatively, the amplified biotin deposit can be detected with avidin-peroxidase complex, that is then contacted with DAB to produce a brown color.

In other examples, signal amplification includes contacting the sample with hydrogen peroxide and a tyramide-HQ conjugate after contacting the sample with an HRP-conjugated tertiary antibody under conditions sufficient for depositing HQ at or near the site of the primary antibody bound to the sample. The sample is then contacted with an enzyme-conjugated antibody (such as an HRP- or AP-conjugated antibody) that specifically binds to HQ. In some examples, this enzyme-conjugated antibody is the same as the HRP-conjugated tertiary antibody. In other examples, the enzyme-conjugated antibody is a different antibody than the HRP-conjugated tertiary antibody. The sample is then contacted with one or more reagents that produce a detectable reaction product in the presence of the enzyme. In some examples, the sample is contacted with an HRP substrate (such as hydrogen peroxide) and a chromogen (such as DAB) that produces a visually detectable product in the presence of HRP. In some examples, signal amplification is carried out using OPTIVIEW Amplification Kit (Ventana Medical Systems, Inc., Tucson, Ariz., Catalog No. 760-099).

B. Scoring Samples as ALK-Positive or ALK-Negative

To score samples as ALK-positive or ALK-negative, an NSCLC sample with detectably labeled ALK (for example, one or more slides, such as 1, 2, 3, 4, or 5 slides) is used. In some examples, the NSCLC sample can be labeled with an antibody specific for ALK and appropriately labeled secondary and/or tertiary antibodies, for example as described in Section A, above. In one non-limiting example, OPTIVIEW DAB IHC Detection Kit and OPTIVIEW Amplification Kit are used as per the manufacturer's instructions (Ventana Medical Systems, Inc., Catalog Nos. 760-700 and 760-099, respectively).

The anti-ALK labeled NSCLC sample (or a digital image thereof) is visually inspected (for example, with or without light microscopy), for example by a pathologist. In some examples, an entire sample (such as an entire tissue section) is visually inspected, for example using light microscopy, for example at about 2×-20× magnification. In other examples, at least one field of view (such as at least 2, 3, 4, or 5 different fields of view) is visually inspected. A field of view is an area of a sample (for example, a tissue section) to be analyzed by microscopy, which is smaller than the entire section or entire digital image of a section. In some examples, a field of view is an area of a sample visible at 2×, 5×, 10×, 20×, 40×, or 60× magnification (such as 2×-20× magnification).

The disclosed methods can be used to identify (for example, score) a tumor as ALK-positive or ALK-negative, for example to provide prognostic information, such as likely responsiveness of NSCLC to an ALK inhibitor. Tumor (for example neoplastic) cells are evaluated for presence of the detectable label (staining), indicating expression of ALK protein in the tumor cells. A sample that has presence of strong granular cytoplasmic staining in tumor cells (any percentage of tumor cells) is identified or scored as being ALK-positive. Strong granular cytoplasmic staining in at least one tumor cell (such as 2, 3, 4, 5, 10, 15, 20, 25, 30, 35, 40, 45, 50, 55, 60, 65, 70, 75, 80, 85, 90, 95, 100, or more tumor cells) in a sample labeled with an anti-ALK antibody is scored as an ALK-positive sample. For example, strong granular staining in about 1-100,000 cells (such as 10-100,000 cells, 1000-100,000 cells, 1000-50,000 cells, 10,000-50,000 cells, 10-50,000 cells, 500-50,000 cells, or about 1000-10,000 cells) in a sample labeled with an anti-ALK antibody is scored as an ALK-positive sample. In some examples, the strong granular cytoplasmic staining is distributed homogeneously throughout the neoplastic portions of the tumor. In other examples, the strong granular cytoplasmic staining is heterogeneously distributed throughout the neoplastic portions of the tumor. In either example, presence of strong granular cytoplasmic staining in neoplastic portions of the tumor (e.g., in at least one or more tumor cells) is scored as ALK-positive.

If strong granular cytoplasmic staining is not present in at least one tumor cell in a sample labeled with an anti-ALK antibody, the sample is scored as an ALK-negative sample. In some examples, an NSCLC sample with no cytoplasmic staining (for example, no staining above background or negative control levels), weak cytoplasmic staining, and/or moderate cytoplasmic staining in tumor cells is scored as an ALK-negative sample, so long as no tumor cells in the sample have strong granular cytoplasmic staining. A sample with weak cytoplasmic staining and/or moderate cytoplasmic staining in any number of tumor cells is scored as ALK-negative, unless at least one tumor cell in the sample with strong granular cytoplasmic staining is present, in which case the sample is scored as ALK-positive.

Methods of determining staining intensity (for example, semi-quantitative IHC methods) are known to one of ordinary skill in the art. In some examples, strong granular cytoplasmic staining includes staining in one or more tumor cells that would be identified as "3+" intensity of staining by one of ordinary skill in the art (for example, utilizing a scale of 0, no staining above background, 1+ weak intensity staining, 2+ moderate intensity staining, and 3+ strong intensity staining). Therefore, in some examples, presence of at least one cell with cytoplasmic staining intensity of 3+(e.g., strong staining) is considered to be an ALK-positive sample. In some examples, presence in a sample of cytoplasmic staining that would be identified as 1+(e.g., weak staining) or 2+(e.g., moderate staining) intensity by one of ordinary skill in the art in any number of tumor cells is scored as an ALK-negative sample, unless there is also at least one tumor cell with strong granular cytoplasmic staining (e.g., 3+ staining intensity) present in the sample.

One of ordinary skill in the art can identify portions of the sample which are neoplastic (e.g., tumor cells) and portions of the sample which are normal tissue or cells, for example based on morphological and/or histological characteristics. In some examples, the sample is stained with H&E (for example the same sample that is labeled with the anti-ALK antibody or an adjacent tissue section) to assist in identifying tissue and cell morphology.

In some examples of the disclosed methods, one or more necrotic tumor areas may be present in a labeled sample. Staining of necrotic tumor areas or necrotic tumor cells (for example, tumor areas with loss of nuclei and inflammatory infiltrate with or without preserved cellular outlines) with the anti-ALK antibody is not considered to be positive staining of tumor cells and is excluded from evaluation of the sample for strong granular cytoplasmic staining of tumor cells. Samples with any intensity staining (including strong intensity staining) of necrotic tumor cells or areas are considered to be ALK-negative, unless there is also at least one tumor cell with strong granular cytoplasmic staining present in the sample.

In other examples of the disclosed methods, staining of non-tumor cells or normal cell elements, even strong granular cytoplasmic staining, is not considered to be positive staining and is excluded from evaluation of the sample. For example, cells of neural origin (such as nerve cells and/or ganglion cells) are known to express ALK (e.g., Iwahara et al., *Oncogene* 14:439-449, 10997). Therefore, staining of neurons or ganglia (or other cells of neural origin) is not included in the evaluation of the sample. Samples with any intensity staining of cells of neural origin are considered to be ALK-negative, unless there is also at least one tumor cell with strong granular cytoplasmic staining present in the sample.

In additional examples, anti-ALK staining of normal mucosa or glandular epithelial cells (even strong granular cytoplasmic staining) is not considered to be ALK positive staining and is excluded from evaluation of the sample. Samples with any intensity staining of normal mucosa or glandular epithelial cells are considered to be ALK-negative, unless there is also at least one tumor cell with strong granular cytoplasmic staining present in the sample. Similarly, anti-ALK staining of alveolar macrophages (for example, light granular cytoplasmic stippling) or infiltrating lymphocytes is not considered to be ALK positive staining and is excluded from evaluation of the sample. Samples with any intensity staining of alveolar macrophages or infiltrating lymphocytes are considered to be ALK-negative, unless there is also at least one tumor cell with strong granular cytoplasmic staining present in the sample.

In further examples, mucin is stained by the anti-ALK antibody and is not considered to be ALK positive staining and is excluded from evaluation of the sample. Samples with any intensity staining of mucin are considered to be ALK-negative, unless there is also at least one tumor cell with strong granular cytoplasmic staining present in the sample.

In some examples, the scoring method also includes comparing the anti-ALK labeled NSCLC sample with one or more controls labeled with the anti-ALK antibody (for example, controls assayed in the same IHC run as the NSCLC sample). In some examples, the control includes a positive control, such as a sample including cells known to be ALK-positive (for example H228 cells). In other examples, the control includes a negative control, such as a sample including cells known to be ALK-negative (for example Calu-3 cells). In some examples, the positive and/or negative control samples are system-level controls to ensure proper functioning of assay reagents and instruments. In one example, the controls include both a positive and a negative control (for example, ALK 2 in 1 Control Slides, Ventana Medical Systems, Inc., Catalog No. 781-4796).

In other examples, the negative control includes an NSCLC sample stained with a negative control antibody. In some examples, the negative control antibody is an antibody that binds specifically to a target antigen that is not endogenously present in an NSCLC sample. In some examples, the negative control antibody is an immunoglobulin, such as a monoclonal antibody. Staining with the negative control antibody can be used to evaluate the level of background staining in a sample from the subject. In some examples, the NSCLC sample stained with the negative control antibody is an NSCLC sample from the same subject (such as an adjacent or serial section from the sample) as the sample stained with the anti-ALK antibody. In other examples, the NSCLC sample stained with the negative control antibody is from a different subject than the sample stained with the anti-ALK antibody.

C. Samples

Methods of obtaining a biological sample from a subject are known in the art. For example, methods of obtaining lung tissue or lung cells are routine. For example, a sample from a lung tumor that contains cellular material can be obtained by surgical excision of all or part of the tumor, by collecting a fine needle aspirate from the tumor, as well as other methods known in the art. In some examples, the sample is obtained from a subject having or suspected to have NSCLC. In particular examples, the sample obtained from the subject includes NSCLC tumor cells, such as at least a portion of an NSCLC tumor. In some examples, the sample from the subject also includes normal (e.g., non-tumor) tissue or cells.

Samples are processed post-collection by fixation and in some examples are wax- (e.g., paraffin-) embedded. Fixatives for mounted cell and tissue preparations are well known in the art and include, without limitation, formalin fixative, 95% alcoholic Bouin's fixative; 95% alcohol fixative; B5 fixative, Bouin's fixative, Karnovsky's fixative (glutaraldehyde), Hartman's fixative, Hollande's fixative, Orth's solution (dichromate fixative), and Zenker's fixative (see, e.g., Carson, *Histotechology: A Self-Instructional Text*, Chicago: ASCP Press, 1997). ALK staining intensity may decrease if particular fixatives (such as 95% alcohol, AFA, B5, or Prefer) are used. ALK staining may also decrease if tissue samples are not fixed within a short time of collection or are not fixed for a sufficient period of time. In particular examples, the sample is fixed in neutral buffered formalin (such as 10% neutral buffered formalin) or zinc formalin. In some examples, the sample is fixed for at least about 6 hours (for example, about 6-48 hours, 12-24 hours or about 6, 12, 16, 18, 24, 36, or 48 hours). In additional examples, the sample is placed in fixative within about 6 hours of collection (for example, within about 15 minutes, 30 minutes, 1, 2, 3, 4, 5, or 6 hours).

In some examples, the sample can be a fixed, wax-embedded lung tissue sample, such as a fixed, wax-embedded lung tissue sample including NSCLC tumor. In some examples, the sample is a lung tissue section including NSCLC tumor that is stained with hematoxylin and eosin (H&E).

In some examples, the sample is a lung tissue section including NSCLC tumor labeled with a primary antibody specific for ALK, which may be labeled directly or indirectly (e.g., with a labeled secondary antibody), which in some examples is further stained with H&E.

In some examples, the sample (or a fraction thereof) is present on a solid support. Solid supports bear the biological sample and permit the convenient detection of components (e.g., proteins) in the sample. Exemplary supports or substrates include microscope slides (e.g., glass microscope slides or plastic microscope slides), coverslips (e.g., glass coverslips or plastic coverslips), tissue culture dishes, multi-well plates, membranes (e.g., nitrocellulose or polyvinylidene fluoride (PVDF)) or BIACORE™ chips.

D. Methods of Treatment

The disclosed embodiments can further include selecting subjects for treatment with an ALK inhibitor, for example if the sample from the subject is scored as ALK-positive. Additionally, the disclosed methods can further include administering an ALK inhibitor to the subject if the sample from the subject is scored as ALK-positive.

In some examples, the ALK inhibitor is a small molecule inhibitor, such as crizotinib (Pfizer, New York, N.Y.), AP26113 (Ariad Pharmaceuticals, Cambridge, Mass.), CH5424802 (Chugai Pharmaceutical, Tokyo, Japan), LDK378 (Novartis, Basel, Switzerland), ASP3026 (Astellas Pharma, Northbrook, Ill.), X-396 (Xcovery, West Palm Beach, Fla.), or retaspimycin (Infinity Pharmaceuticals, Cambridge, Mass.). Additional ALK inhibitors include 3-39 (Novartis), GSK1838705A (GlaxoSmithKline, Boston, Mass.), and CEP-28122 (Cephalon, Frazer, Pa.). In another example, an ALK inhibitor is an anti-ALK antibody, such as a humanized anti-ALK antibody.

In some examples, the disclosed methods include providing a therapeutically effective amount of the ALK inhibitor to the subject (such as a subject having ALK-positive NSCLC). Methods and therapeutic dosages of such agents and treatments are known to those of ordinary skill in the art, and for example, can be determined by a skilled clinician. In a non-limiting example, a therapeutically effective amount of crizotinib is administered to a subject having an NSCLC tumor that is identified as ALK-positive. In some examples, a therapeutically effective amount of crizotinib can be about 50-2000 mg/day (such as about 50, 100, 150, 200, 250, 300, 400, 500, 600, 700, 800, 900, 1000, 1100, 1200, 1300, 1400, 1500, 1600, 1700, 1800, 1900, 2000 mg/day), administered orally in one or two doses per day. In some examples, the methods include orally administering 200 mg of crizotinib to the subject once or twice per day if the sample from the subject is scored as ALK-positive. In other examples, the methods include orally administering 250 mg of crizotinib to the subject once or twice per day if the sample from the subject is scored as ALK-positive. Dosages and dosing schedules of crizotinib for a subject can be determined by a skilled clinician, taking into account additional factors such as tumor site, tumor stage, tumor grade, patient treatment history, patient performance and nutritional status, concomitant health problems, social and logistic factors, previous primary tumors, and patient preference. Crizotinib may be administered on a continuous dosing schedule or administered for one or more cycles (for example, one or more cycles of 21-28 days). Treatment may repeat every 21-28 days if administered in cycles.

In some examples, the subject is also administered one or more additional chemotherapeutic agents in combination with the ALK inhibitor. Additional chemotherapeutic agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as podophyllum (for example, etoposide, and teniposide), taxane (for example, docetaxel and paclitaxel), vinca (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, rifampicin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, pertuzumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, axitinib, bexarotene, bevacizumab, bortezomib, celecoxib, denileukin diftitox, erlotinib, estramustine, gefitinib, hydroxycarbamide, imatinib, lapatinib, pazopanib, pentostatin, masoprocol, mitotane, pegaspargase, tamoxifen, sorafenib, sunitinib, vemurafinib, vandetanib, and tretinoin. Selection and therapeutic dosages of such agents are known to those skilled in the art, and can be determined by a skilled clinician.

In other examples, the disclosed methods include providing surgery, radiation therapy, and/or chemotherapeutics to the subject in combination with the ALK inhibitor (for example, sequentially, substantially simultaneously, or simultaneously). Methods and therapeutic dosages of such agents and treatments are known to those skilled in the art, and can be determined by a skilled clinician.

The present disclosure is illustrated by the following non-limiting Examples.

Example 1

ALK Immunohistochemistry Protocol

This example describes methods of ALK IHC for identifying ALK-positive NSCLC samples.

Formalin-fixed paraffin embedded NSCLC tissue sections were stained with anti-ALK D5F3 rabbit monoclonal antibody (Ventana Medical Systems, Catalog No. 790-4794). A separate tissue section from each NSCLC sample was stained with Rabbit Monoclonal Negative Control Ig (Ventana, Catalog No. 790-4795). Slides were also stained with hematoxylin and eosin (H&E) to distinguish morphology. ALK 2 in 1 control slides (Ventana Catalog No. 781-4796) were used as system level positive and negative controls. Slides were stained using a Ventana BENCHMARK XT automated slide stainer and OPTIVIEW DAB IHC Detection Kit (Ventana, Catalog No. 760-700) and OPTIVIEW Amplification Kit (Ventana Catalog No. 760-099) with the staining protocol shown in Table 1. The same protocol and reagents were also tested using a Ventana BENCHMARK GX automated slide stainer.

TABLE 1

Staining Protocol for anti-ALK (D5F3) and Rabbit Monoclonal Negative Control Ig with OPTIVEIW DAB IHC Detection Kit and OPTIVIEW Amplification Kit

| Procedure Type | Method |
| --- | --- |
| Deparaffinization | Selected |
| Cell Conditioning (antigen unmasking) | Cell Conditioning 1 |
| | 92 minutes, 100° C. |
| Pre-Primary Peroxidase Inhibitor | Selected |
| Antibody (Primary) | 16 minutes, 37° C. |
| OPTIVIEW HQ Univ Linker | 12 minutes |
| OPTIVIEW HRP Multimer | 12 minutes |
| OPTIVIEW Amplification | Selected |
| OV AMP H2O2, OV Amplifier | 8 minutes |
| OV AMP Multimer | 8 minutes |
| Counterstain | Hematoxylin II, 4 minutes |
| Post Counterstain | Bluing, 4 minutes |

Example 2

Evaluation of Immunohistochemical Results

This example describes exemplary methods of evaluating or scoring ALK IHC results to determine whether an NSCLC sample is positive or negative for ALK.

ALK IHC was performed with the anti-ALK D5F3 antibody as described in Example 1. Neoplastic cells labeled with the ALK IHC assay were evaluated for presence or absence of DAB signal. The matched negative control slide was used to assess non-specific background staining and degree of background staining known to occur due to specific tissue elements (alveolar macrophages, neural cells, glandular epithelial cells, cells in lymphocytic infiltrate). Samples were determined to be positive or negative for ALK based on the scoring algorithm in Table 2.

TABLE 2

Scoring criteria for determination of ALK status in NSCLC

| Clinical Interpretation | Staining Description |
|---|---|
| Positive for ALK | Presence of strong granular cytoplasmic staining in tumor cells (any percentage of positive tumor cells). Known staining elements should be excluded, including: light cytoplasmic stippling in alveolar macrophages cells of neural origin (nerve and ganglion cells) glandular epithelial staining cells within lymphocytic infiltrate Some background staining may also be observed within normal mucosa in NSCLC (including mucin) and in necrotic tumor areas, which should also be excluded from the clinical evaluation |
| Negative for ALK | Absence of strong granular cytoplasmic staining in tumor cells |

Figure 2A:
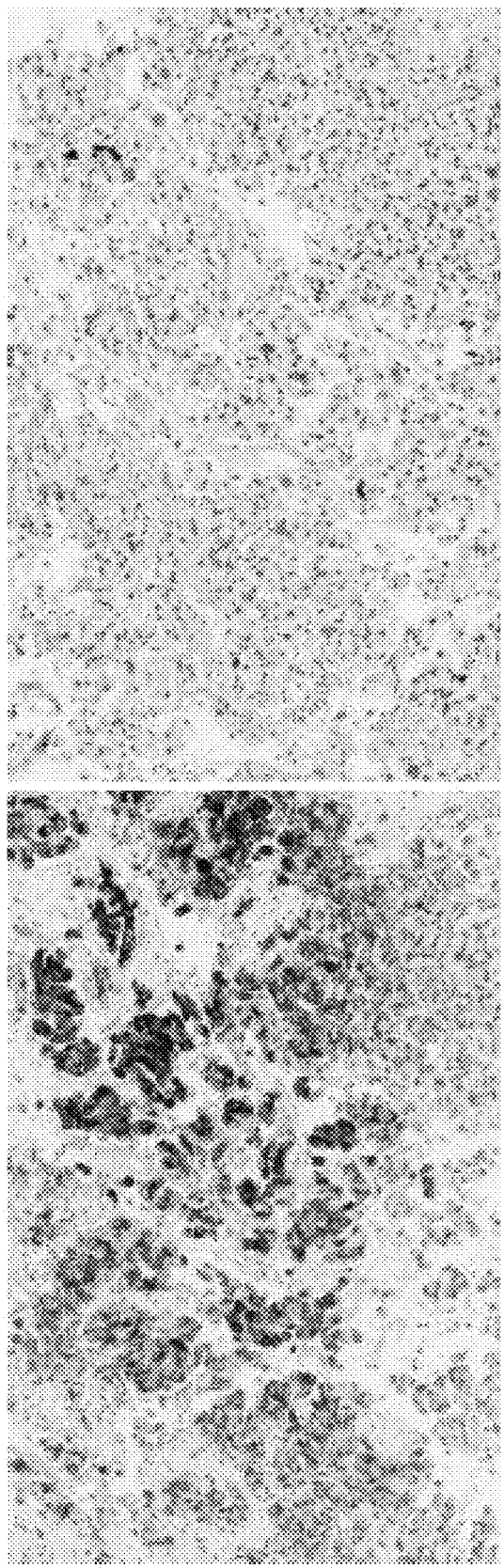
FIGS. 2A-C are digital images of three exemplary ALK-positive cases showing heterogeneous ALK IHC expression on anti-ALK (D5F3) staining (left panels) and matched rabbit monoclonal negative control Ig staining (right panels). Strong cytoplasmic staining is present in the anti-ALK stained samples, but the intensity varies.
Figure 2B:
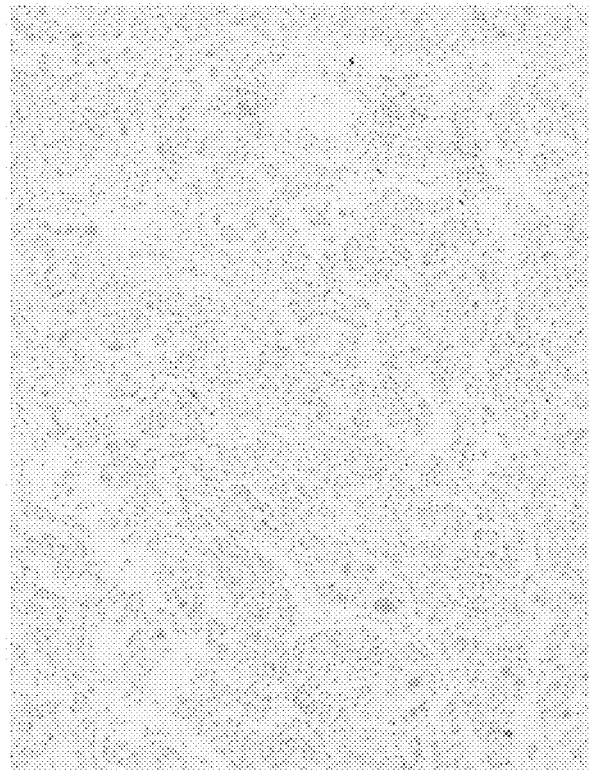
Figure 2B:
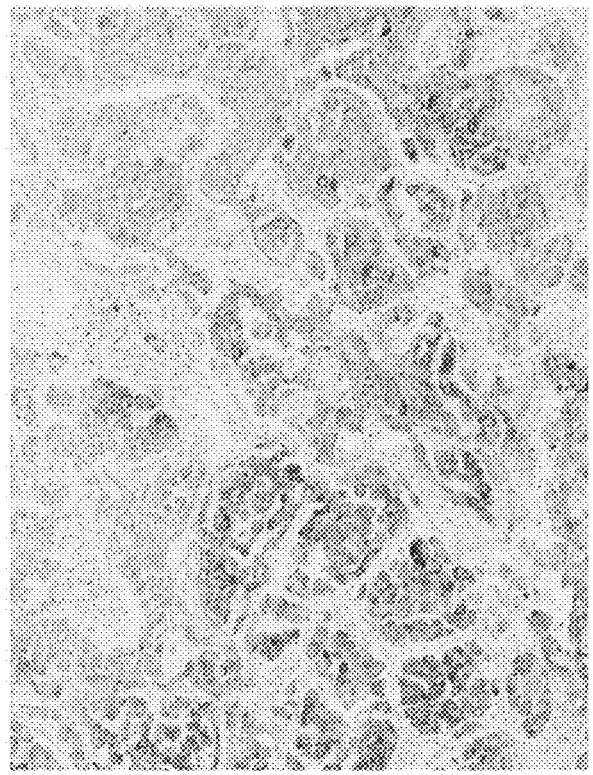
Figure 2C:
Figure 2C:
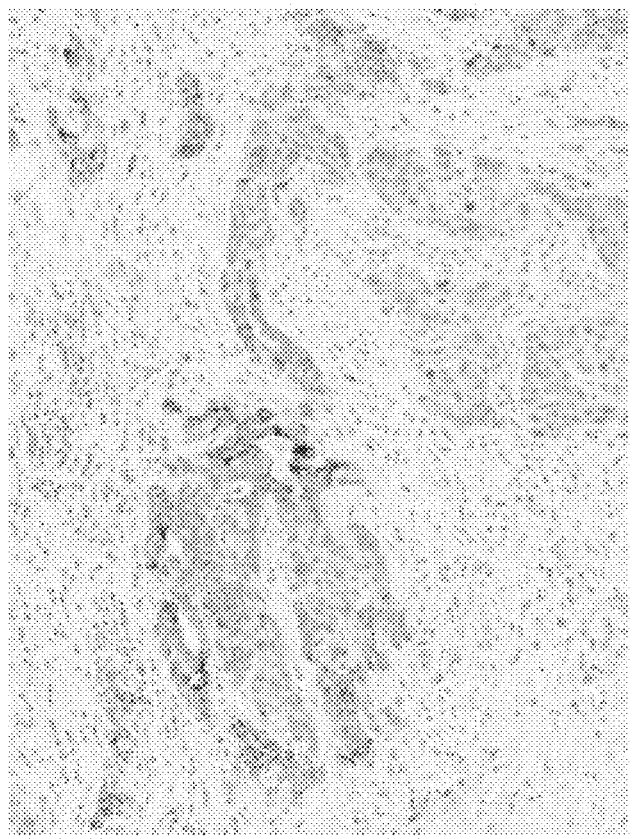

Positive for ALK:

Positive cases stained with the IHC assay described in Example 1 typically displayed a strong, granular cytoplasmic signal. Any sample that had strong cytoplasmic staining (such as 3+ staining in conventional IHC scoring) in any number of tumor cells was scored as positive. In the majority of positive cases, the signal was distributed homogeneously, having a uniform level of intensity throughout the neoplastic portions of the tumor. In some positive cases, the signal was more heterogeneous in staining intensity. Examples of homogeneous ALK IHC expression are shown in FIGS. 1A and B. Examples of heterogeneous ALK IHC expression are shown in FIGS. 2A-C.

Figure 3:
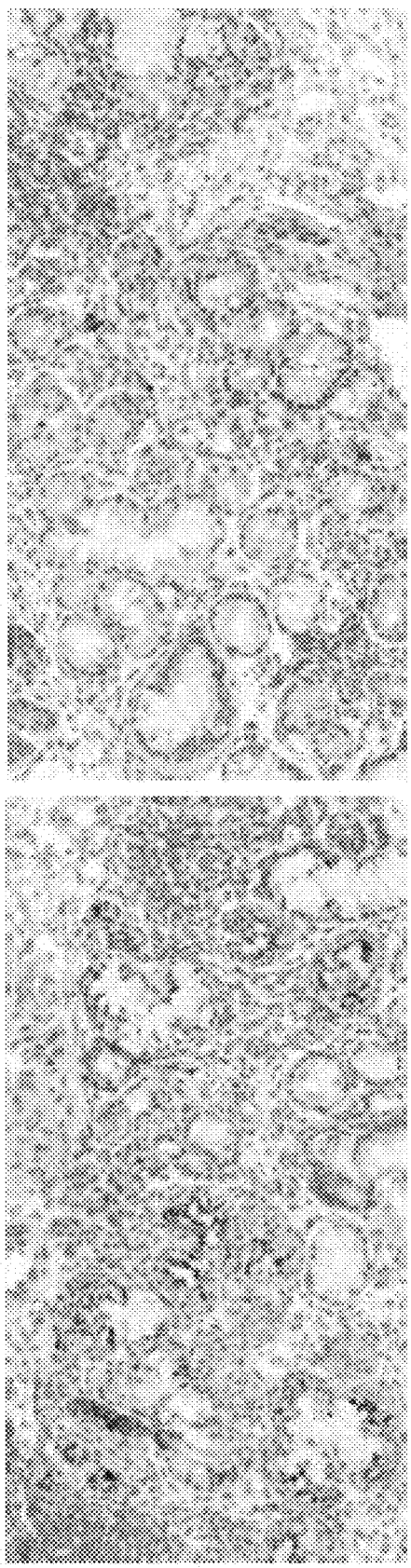
FIG. 3 is a digital image showing punctate granular staining in glandular epithelial cells in a sample stained with anti-ALK (D5F3) antibody (left panel). Less evident staining of glandular epithelial cells was seen in the matched rabbit monoclonal negative control Ig slide (right panel). The glandular epithelial staining was present in normal tissue elements, but not cancer cells and was excluded in slide interpretation.
Figure 4A:
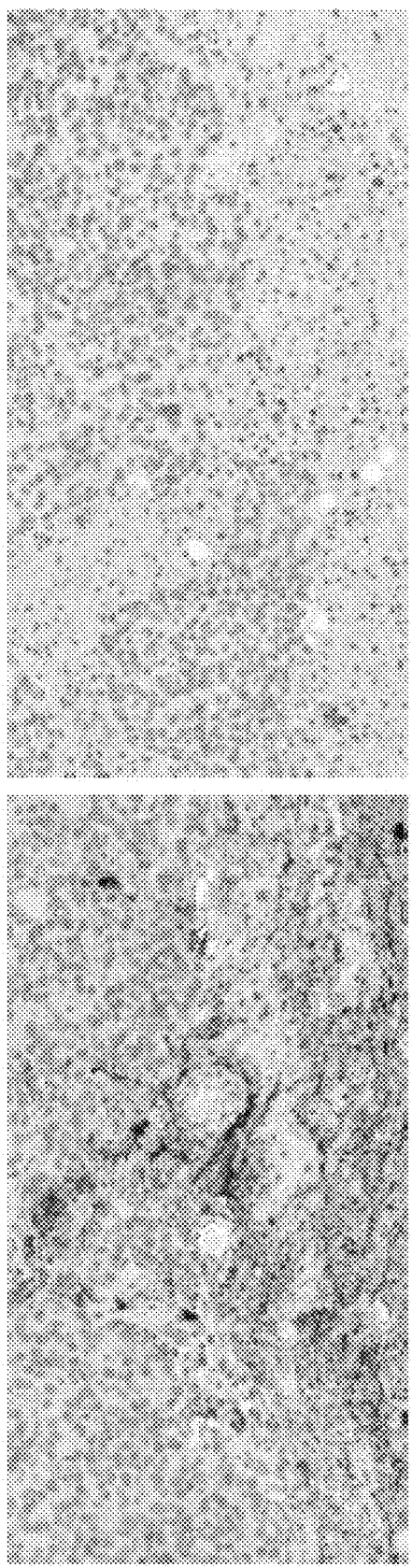
FIG. 4A is a digital image showing staining of apparent neuronal tissue elements in a sample stained with anti-ALK (D5F3) antibody (left panel) and the lack of staining in the matched rabbit monoclonal negative control Ig slide (right panel).
Figure 4B:
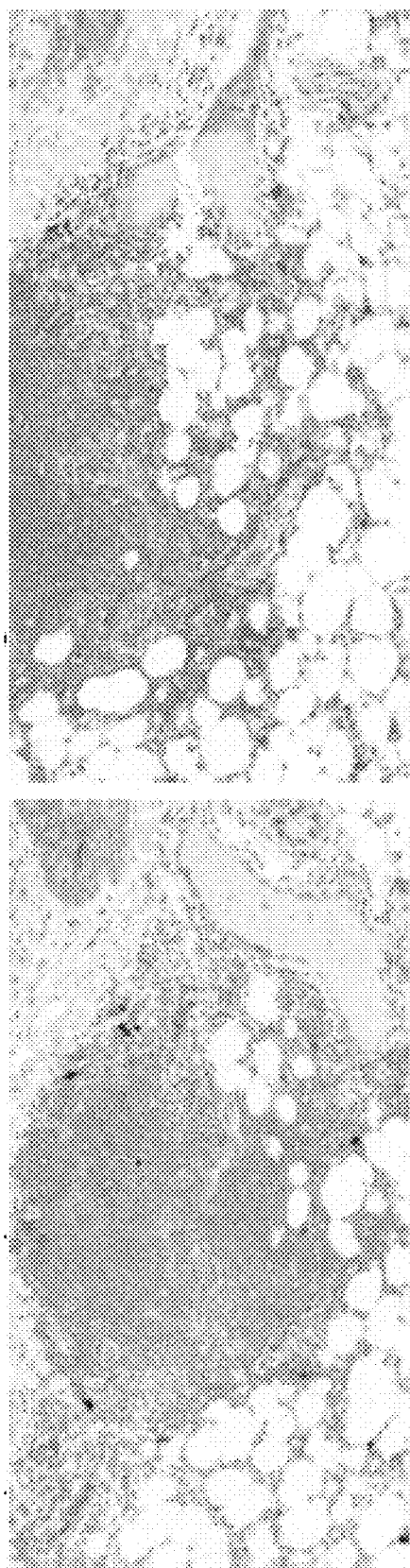
FIG. 4B is a digital image showing staining of neural tissue in a sample stained with anti-ALK (D5F3) antibody (left panel) and in the matched rabbit monoclonal negative control Ig slide (right panel). The staining was excluded in slide interpretation because it was present in normal tissue elements or cells.
Figure 5:
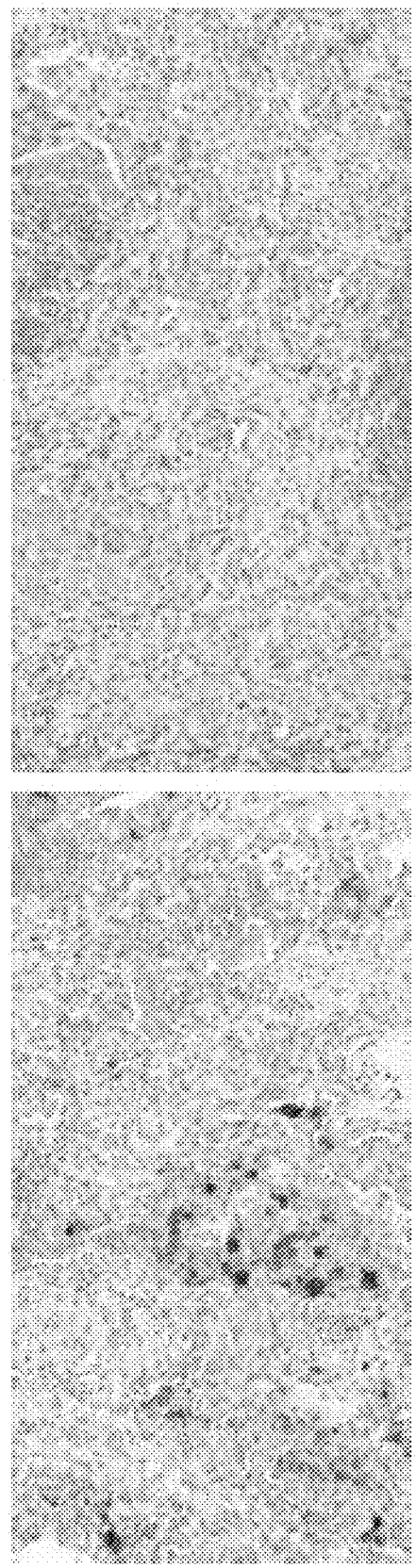
FIG. 5 is a digital image showing granular stippling present in alveolar macrophages in a sample stained with anti-ALK (D5F3) antibody (left panel) and the lack of staining in the matched rabbit monoclonal negative control Ig slide (right panel). This staining was excluded in slide interpretation because it was present in normal cells, not tumor cells.
Figure 6A:
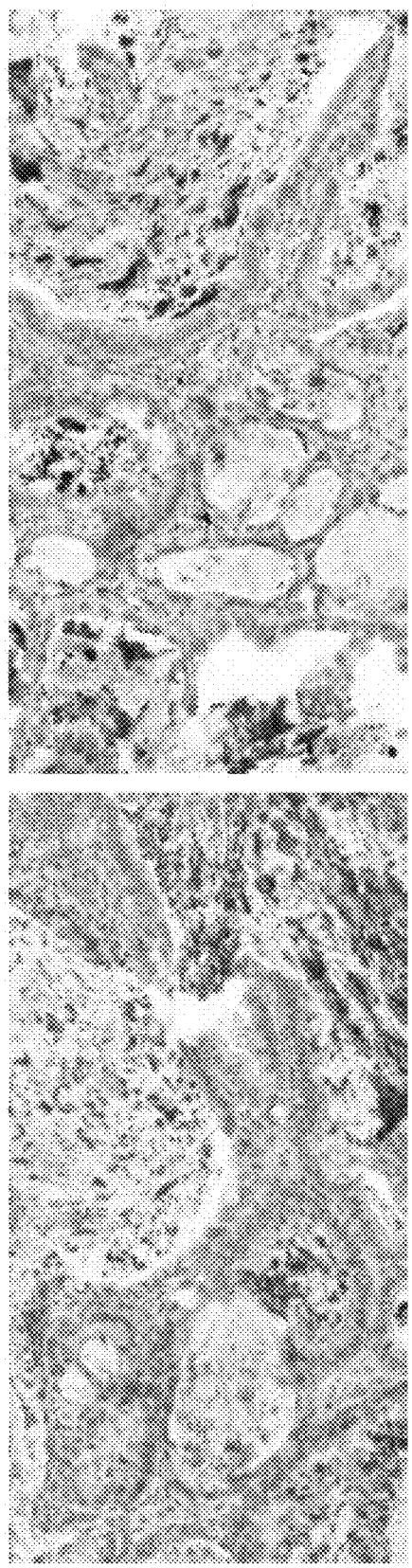
FIG. 6A is a digital image showing staining of mucin in a sample stained with anti-ALK (D5F3) antibody (left panel) and in the matched rabbit monoclonal negative control Ig slide (right panel). There was no staining in the normal tissue and tumor cells, therefore this sample was interpreted to be ALK-negative.
Figure 6B:
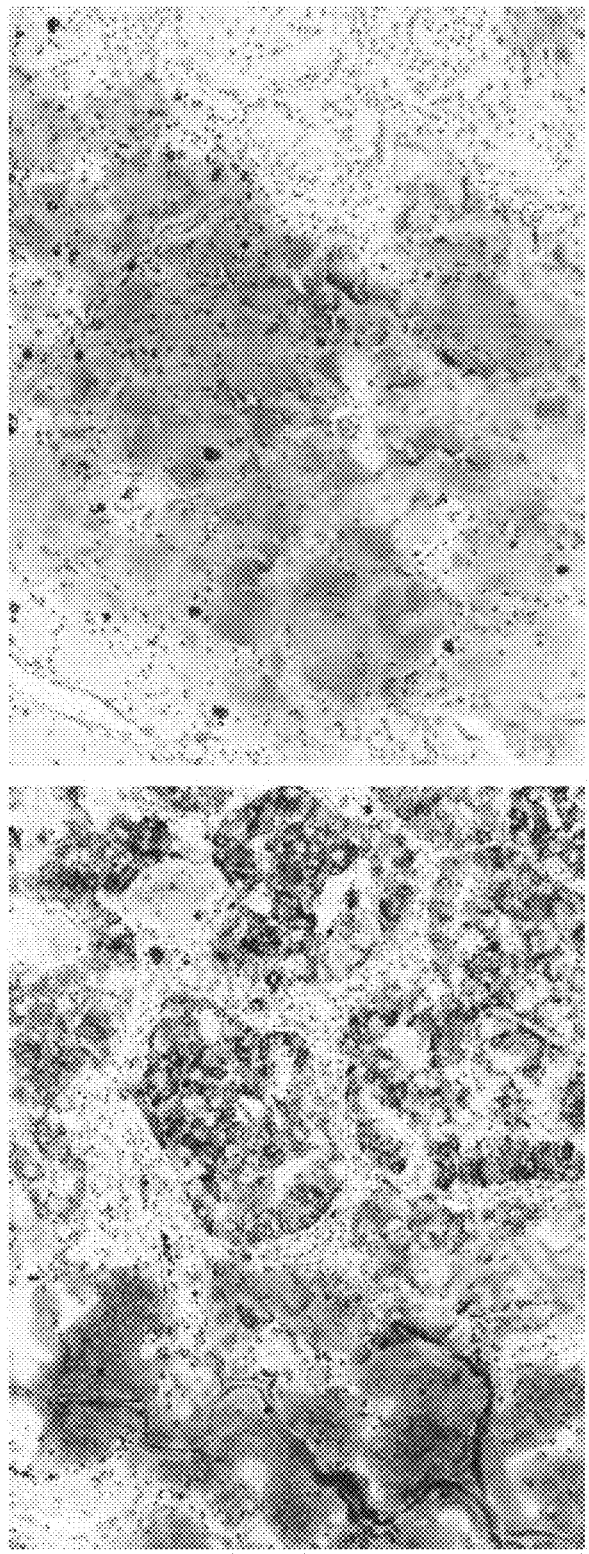
FIG. 6B is a digital image showing staining of mucin in a sample stained with anti-ALK (D5F3) antibody (left panel) and in the matched rabbit monoclonal negative control Ig slide (right panel). This sample was interpreted to be ALK-positive because the normal tissue was negative but the tumor cells were stained.
Figure 7A:
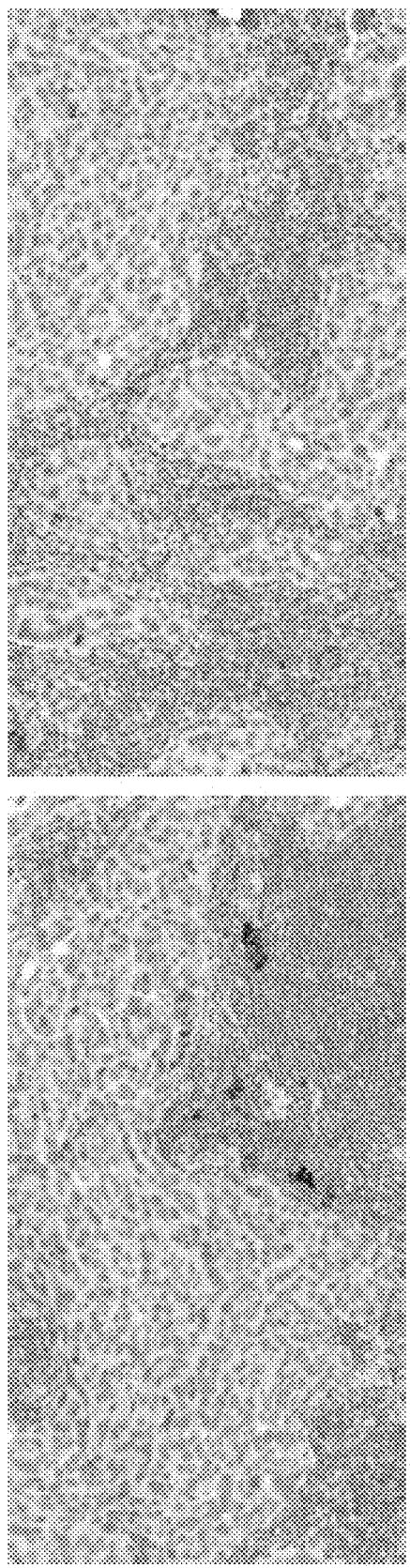
FIGS. 7A and B are digital images showing staining of some lymphocytes in a sample stained with anti-ALK (D5F3) antibody (left panels) and less evident (FIG. 7A) or negative (FIG. 7B) staining in the matched rabbit monoclonal negative control Ig slide (right panels). This staining was excluded in slide interpretation because it was present in normal cells.
Figure 7B:
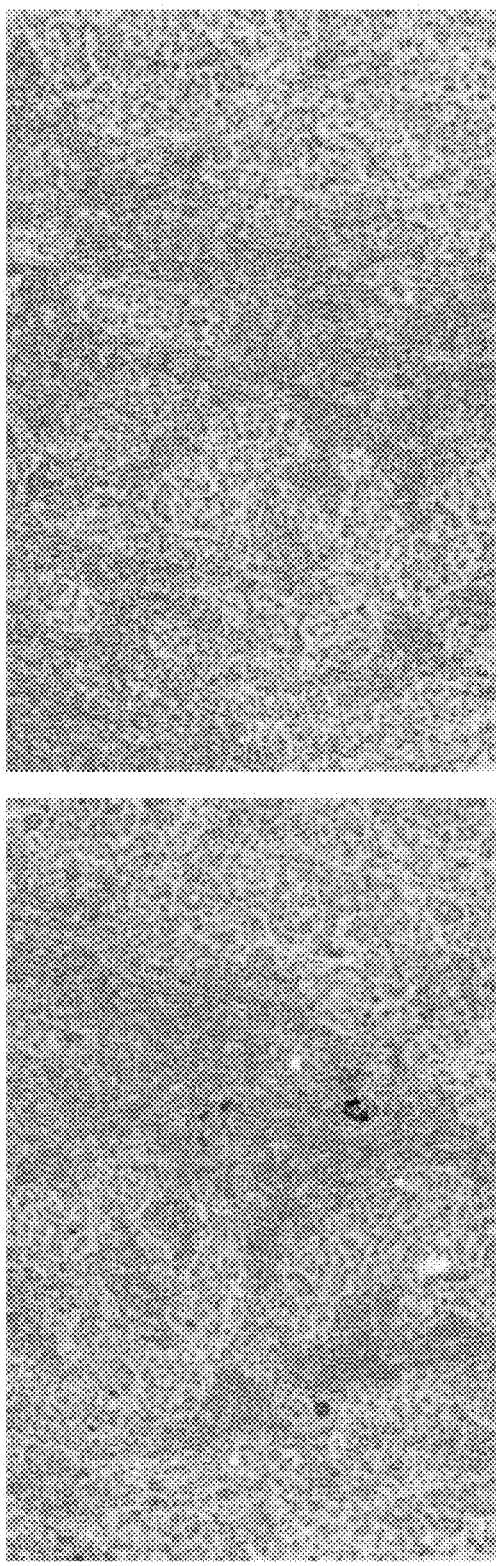

Some background staining was observed within normal mucosa in NSCLC samples, as well as in necrotic tumor areas. This staining was not evaluated as ALK-positive staining. Additionally, staining was noted in neural cells (including nerve or ganglion cells), glandular epithelial cells, alveolar macrophages, and cells in lymphocytic infiltration or lung metastases to lymph nodes. Staining of mucin was also noted in some samples. All of these were excluded when determining whether the sample was ALK-positive. Examples of these excluded types of ALK staining are shown in FIG. 3 (glandular epithelial cell staining), 4A and B (neural cell staining), 5 (alveolar macrophage staining), 6A and B (mucin staining), and 7A and B (lymphocyte staining).

Figure 8A:
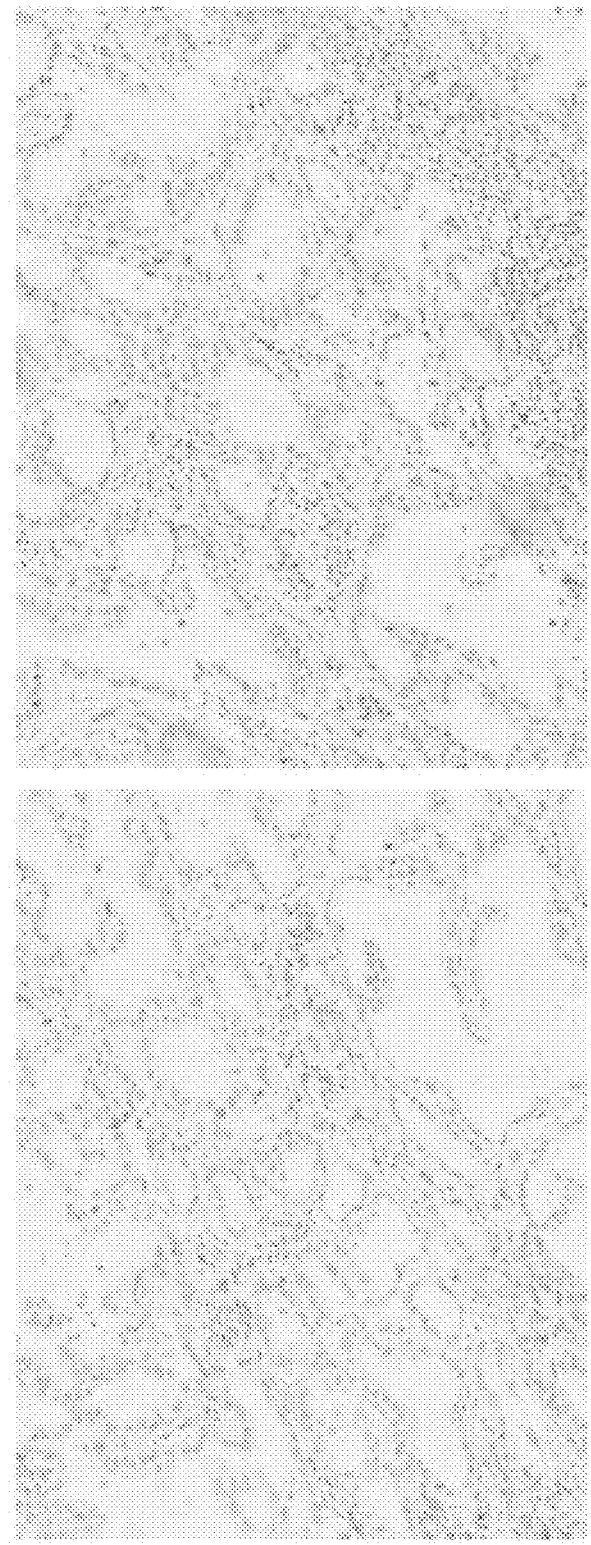
FIGS. 8A and B are digital images of two exemplary ALK-negative cases showing absence of ALK IHC expression in tumor cells on anti-ALK (D5F3) staining (left panels) and matched rabbit monoclonal negative control Ig staining (right panels).
Figure 8B:
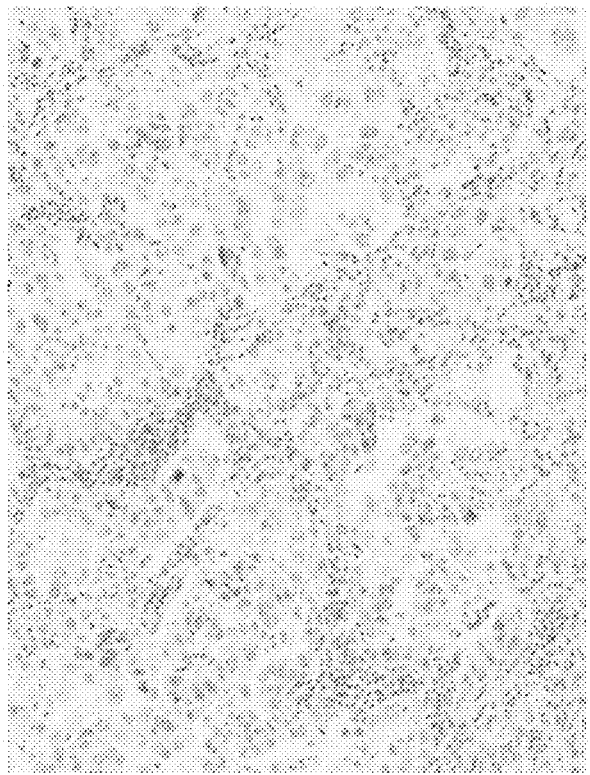
Figure 8B:
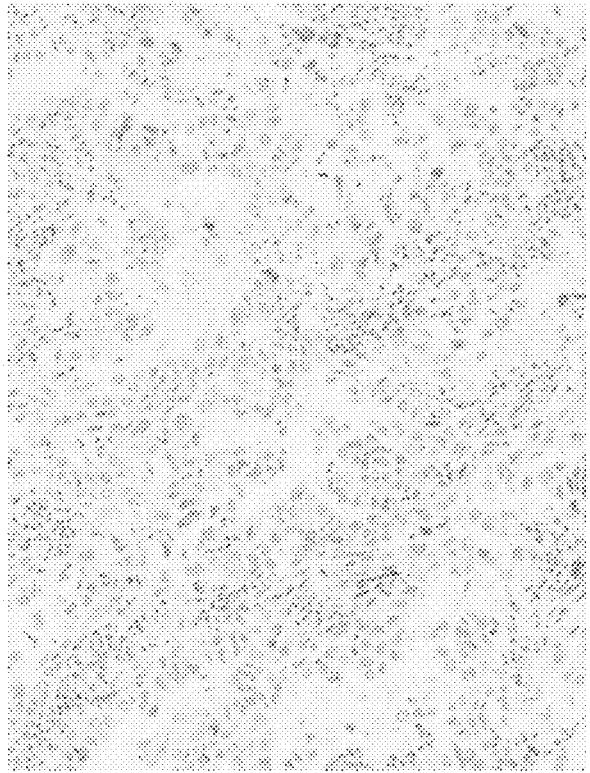
Figure 9A:
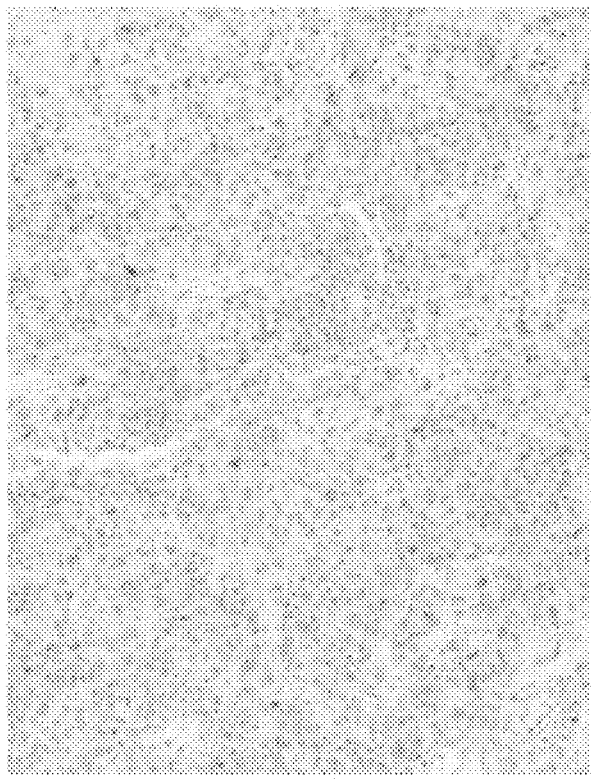
FIGS. 9A and B are digital images of exemplary ALK-negative cases showing weak granular cytoplasmic staining on both anti-ALK (D5F3) staining (left panels) and matched rabbit monoclonal negative control Ig staining (right panels).
Figure 9A:
Figure 9B:
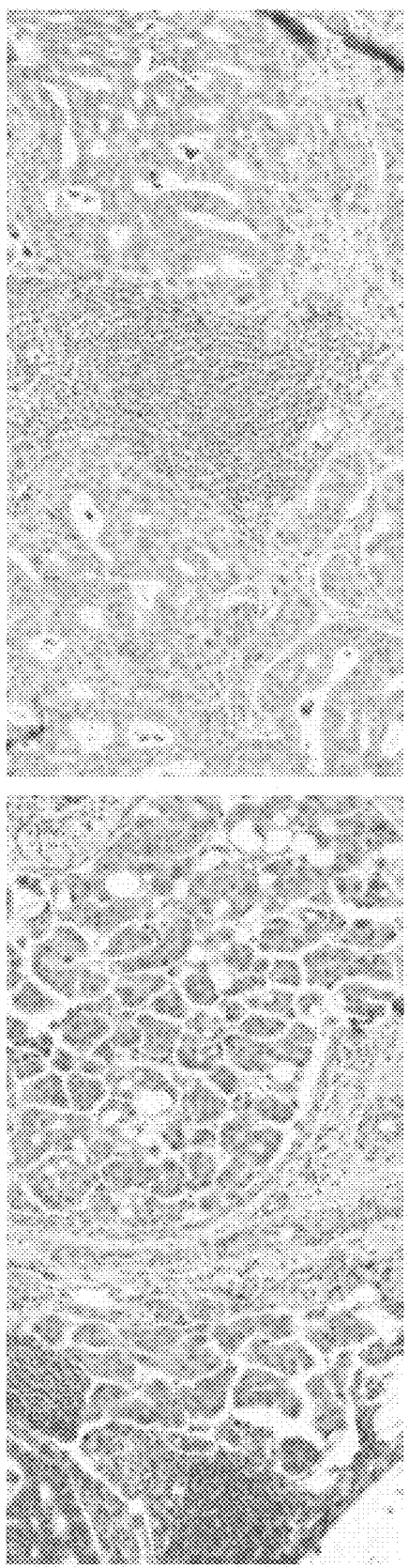
Figure 10A:
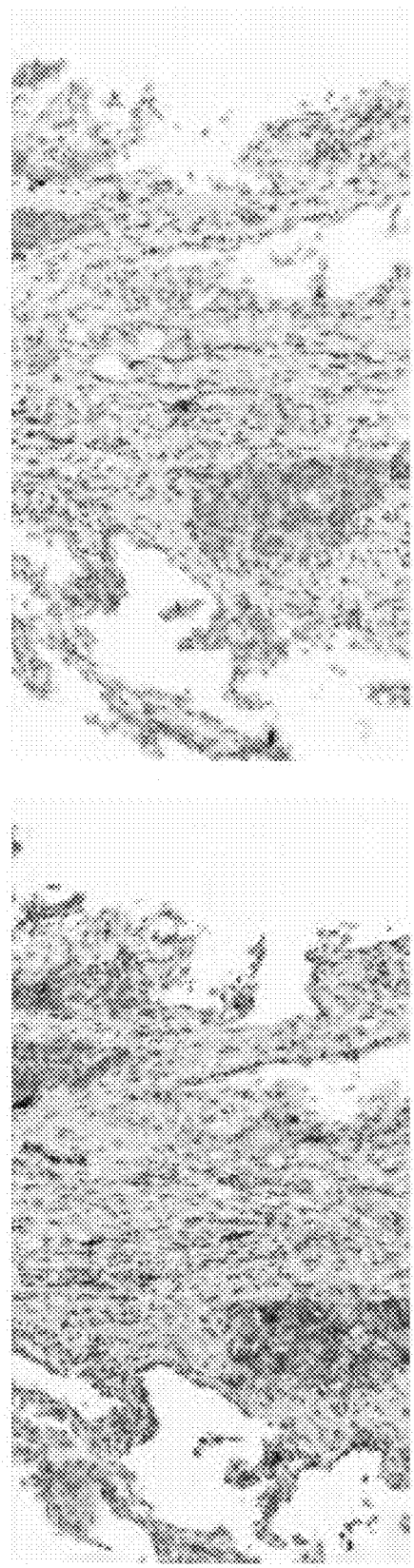
FIGS. 10A-D are digital images of exemplary ALK-negative cases showing cytoplasmic staining on anti-ALK (D5F3) staining (left panels), which is more notable than on the matched rabbit monoclonal negative control Ig staining (right panels). The cases were interpreted as ALK-negative due to the lack of strong cytoplasmic staining.
Figure 10B:
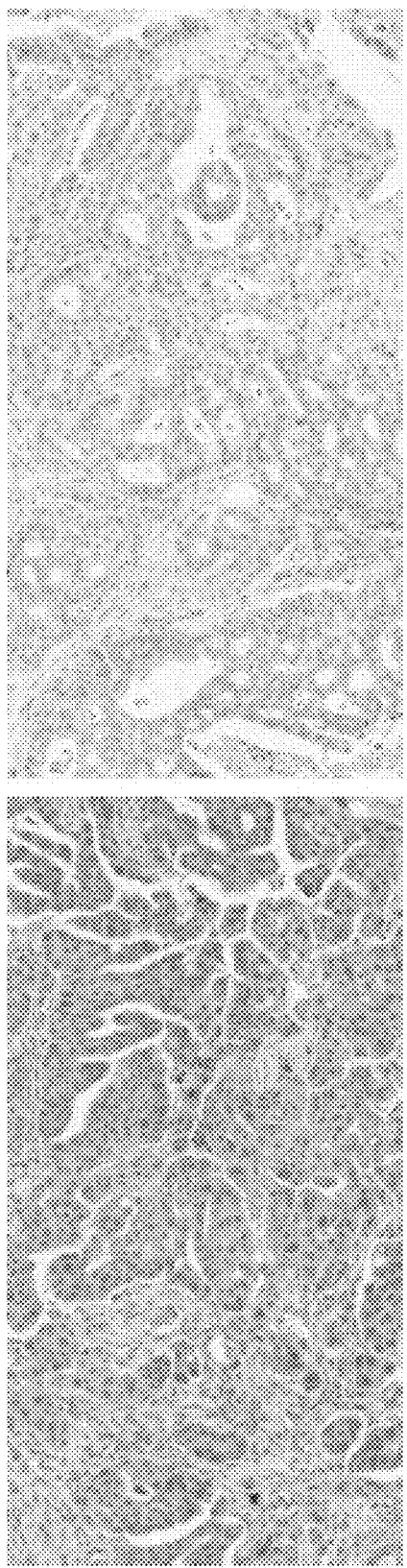
Figure 10C:
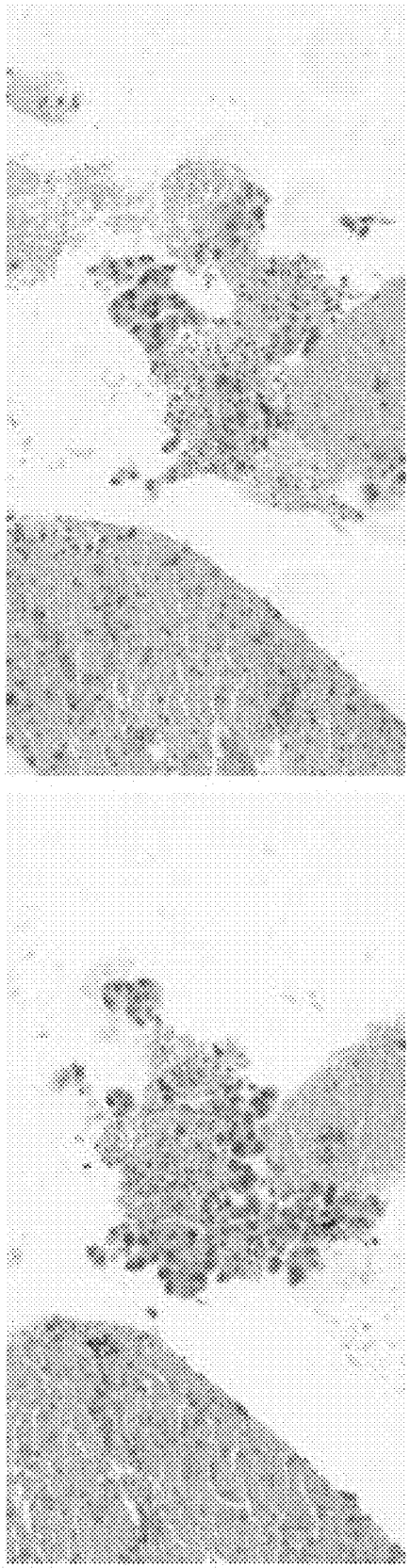
Figure 10D:
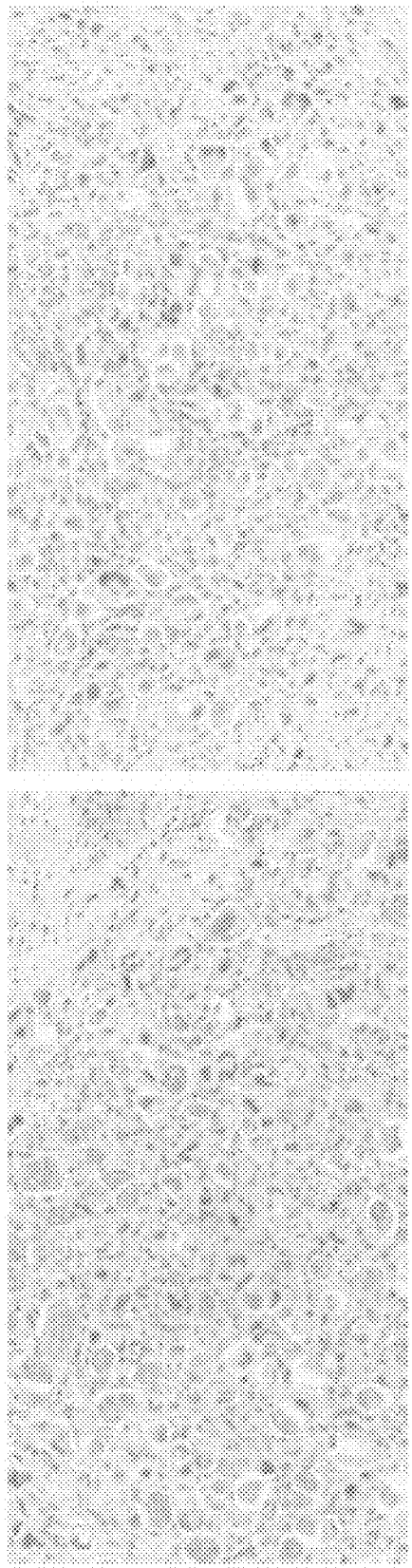

Negative for ALK:

The majority of ALK-negative cases exhibited an absence of DAB signal above background staining from the matched negative control slide (FIGS. 8A and B). However, a minority of negative cases displayed a weak, diffuse granular cytoplasmic pattern that was detected above background staining observed on the matched negative control slide (FIGS. 9A and B). These cases were estimated to represent about 1-2% of ALK-negative cases and were negative by confirmatory FISH analysis.

Figure 11:
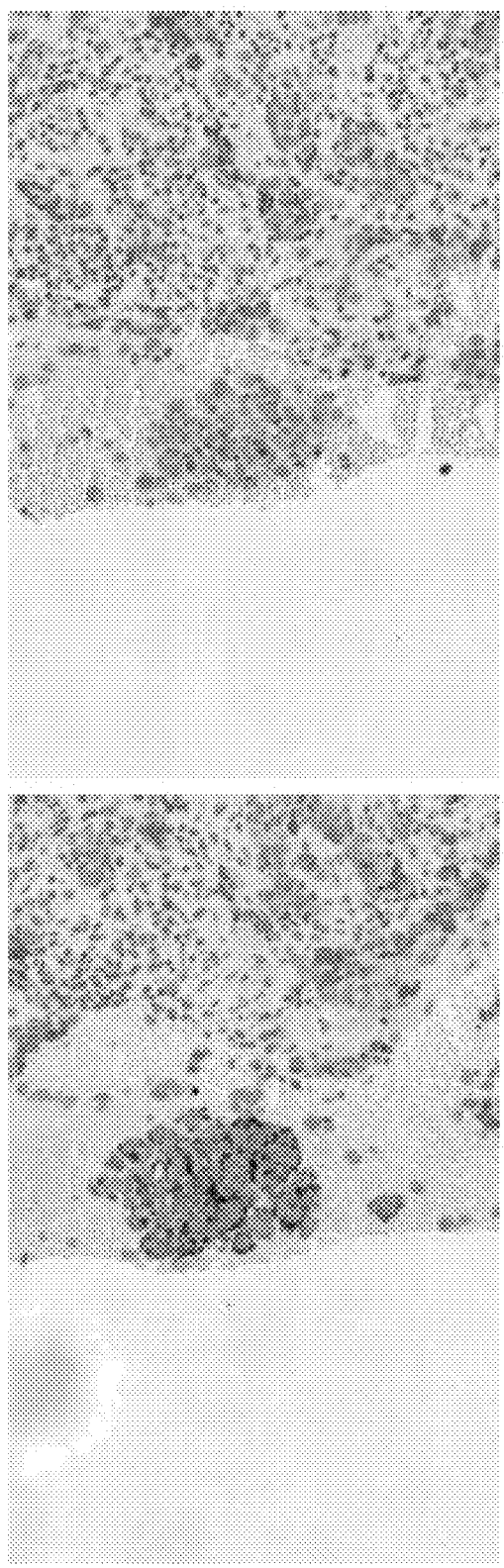
FIG. 11 is a digital image of membrane/cytoplasmic staining in a sample stained with anti-ALK (D5F3) antibody (left panel) and the matched rabbit monoclonal negative control Ig slide (right panel). Although staining was more prevalent on the slide stained with anti-ALK antibody than the negative control, the result was interpreted as ALK-negative because it was not strong granular cytoplasmic staining.

In a few cases, cytoplasmic staining on the slide stained with the anti-ALK (D5F3) antibody was more notable than on the negative control slide. However, these cases did not exhibit strong cytoplasmic staining, and were therefore determined to be ALK-negative (FIG. 10A-D). In another case, membrane/cytoplasmic staining was observed in a slide stained with the anti-ALK antibody (FIG. 11). This sample was determined to be ALK-negative due to the lack of strong granular cytoplasmic staining.

Example 3

Concordance of Immunohistochemical Results with FISH

This example demonstrates the concordance of the ALK IHC scoring method described in Example 2 with ALK break-apart FISH for determining ALK status of NSCLC samples.

Three cohorts were used to compare the staining results from the anti-ALK (D5F3) Rabbit Monoclonal Primary Antibody with ALK FISH in terms of ALK clinical status. The cohorts included a range of human NSCLC tissue samples from primary and metastatic tumors, including resections, needle biopsies, bronchial biopsies, and formalin-fixed, paraffin-embedded (FFPE) cell blocks from fine needle aspirates. IHC was carried out as described in Example 1. All studies were scored using the scoring algorithm in Example 2 (described in Table 2). Break apart FISH data was obtained using the VYSIS ALK Break Apart FISH Probe Kit (Abbott Laboratories, Abbott Park, Ill.) according to the manufacturer's protocols.

Concordance Study 1

A study was conducted in an external laboratory comparing the anti-ALK (D5F3) Rabbit Monoclonal Primary Antibody with retrospective ALK break apart FISH data (Cleveland Clinic Foundation). The external site stained about 100 NSCLC cases using the anti-ALK (D5F3) Rabbit Monoclonal Primary Antibody on a BenchMark XT instrument. The anti-ALK IHC assay demonstrated >98% overall percent agreement with the retrospective ALK break apart FISH data on this NSCLC sample cohort. The results are detailed in Tables 3 and 4. Of the 100 cases, 86 had available FISH data and sufficient tumor present for comparison with the ALK IHC result. The preparation of the tissue specimens for this study was not verified as to fixation conditions (time to fixation after collection, time of fixation).

TABLE 3

Anti-ALK D5F3 IHC compared to break apart FISH

| Anti-ALK D5F3 | Break Apart FISH | | Total |
|---|---|---|---|
| | Positive | Negative | |
| Positive | 10 | 0 | 10 |
| Negative | 1 | 75 | 76 |
| Total | 11 | 75 | 86 |

TABLE 4

Percent overall, positive, and negative agreement rates for anti-ALK D5F3 IHC compared to break apart FISH

| Rate | n/N | % | 95% CI[a] |
|---|---|---|---|
| Overall Percent Agreement | 85/86 | 98.8 | 93.7, 99.8 |
| Positive Percent Agreement | 10/11 | 90.9 | 62.3, 98.4 |
| Negative Percent Agreement | 75/75 | 100.0 | 95.1, 100.01 |

[a]Two-sided 95% confidence interval calculated using the score method

Concordance Study 2

This study was conducted in a second external laboratory comparing the anti-ALK (D5F3) Rabbit Monoclonal Primary Antibody with ALK break apart FISH data on 73 NSCLC cases (cut within one week of staining). The external site stained the cases using the anti-ALK (D5F3) Rabbit Monoclonal Primary Antibody on a BenchMark XT instrument as described in Example 1. The VENTANA ALK IHC assay demonstrated >93% overall percent agreement with the retrospective ALK break apart FISH data on this NSCLC sample cohort. The results are detailed in Tables 5 and 6.

TABLE 5

Anti-ALK D5F3 IHC compared to break apart FISH

| Anti-ALK D5F3 | Break Apart FISH | | |
|---|---|---|---|
| | Positive | Negative | Total |
| Positive | 2 | 4 | 6 |
| Negative | 0 | 56 | 56 |
| Total | 2 | 60 | 62 |

TABLE 6

Percent overall, positive, and negative agreement rates for anti-ALK D5F3 IHC compared to break apart FISH

| Rate | n/N | % | 95% CI$^a$ |
|---|---|---|---|
| Overall Percent Agreement | 58/62 | 93.5 | 84.6-97.5 |
| Positive Percent Agreement | 2/2 | 100 | 34.2-100.0 |
| Negative Percent Agreement | 56/60 | 93 | 84.1-97.4 |

$^a$Two-sided 95% confidence interval calculated using the score method

Of the four discordant (FISH negative, ALK IHC positive) cases, additional unstained slides were tested with another ALK IHC assay (different clone and detection system). Three of the four cases agreed with the anti-ALK (D5F3) IHC assay in terms of ALK IHC staining detected.

There were also 10 cases where FISH results were undetermined or was not performed. Four of these cases were positive by the anti-ALK (D5F3) IHC assay and the other ALK clone, and six were negative by ALK IHC. There was one case that was positive by FISH but not enough sample was available to stain with IHC.

Concordance Study 3

In this study, about 300 cases from an on-going, global clinical study of ALK positive NSCLC patients enrolled with the ALK break apart FISH Probe study were stained with the anti-ALK (D5F3) Rabbit Monoclonal Antibody assay. Of the about 300 cases, some were categorized as "uninformative" by FISH or "FISH assay not performed" and were stained and evaluated for informational purposes only. FISH data for the samples were obtained from central labs participating in the clinical study.

The cases were blinded for FISH status, randomized, and provided to two readers, who evaluated the staining results. Results were compared with the FISH status obtained from the global clinical study. Results of the comparison of ALK IHC with ALK break apart FISH are shown in Table 7. The preparation of the tissue specimens for this study was not verified as to fixation conditions (time to fixation after collection, time of fixation).

TABLE 7

Agreement of anti-ALK D5F3 IHC with ALK break apart FISH as evaluated by two pathologists.

| Anti-ALK D5F3 | | ALK Break Apart FISH | | |
|---|---|---|---|---|
| | Reader | Positive | Negative | Total |
| Reader 1 | Positive | 37 | 13 | 50 |
| | Negative | 11 | 223 | 234 |
| | Total | 48 | 236 | 284 |
| Reader 2 | Positive | 37 | 12 | 49 |
| | Negative | 11 | 225 | 236 |
| | Total | 48 | 237 | 285 |

| | Reader | n/N | Percent | 95% Confidence Interval |
|---|---|---|---|---|
| Reader 1 | Overall Agreement | 260/284 | 91.5 | 87.7, 94.3 |
| | Positive Agreement | 37/48 | 77.1 | 63.5, 86.7 |
| | Negative Agreement | 223/236 | 94.5 | 90.8, 96.8 |
| Reader 2 | Overall Agreement | 262/285 | 91.9 | 88.2, 94.6 |
| | Positive Agreement | 37/48 | 77.1 | 63.5, 86.7 |
| | Negative Agreement | 225/237 | 94.9 | 91.4, 97.1 |

Discrepant cases that were ALK IHC positive, ALK FISH negative:

Four cases were evaluated by at least one reader as ALK IHC positive, FISH negative. Upon consensus review, it was determined that they should be evaluated as IHC negative. These cases had focal cytoplasmic/membrane staining and are considered to be negative, as described in Example 2.

There were nine ALK IHC positive, ALK FISH negative cases that were considered true discrepant cases.

Of the nine discordant cases, seven had unstained slides that were available for additional ALK diagnostic testing (molecular testing and IHC testing using a different clone and detection system). These additional testing results indicated that the majority of discrepant cases favored the positive IHC evaluation for ALK status when ALK FISH was negative. The slides from these cases were cut more than three months prior to staining, which may decrease sensitivity of the IHC assay.

Discrepant cases that were ALK IHC negative, ALK FISH positive:

There were 11 cases that were positive by FISH but negative by the anti-ALK IHC assay. Ten of these cases had unstained slides that were available for the additional ALK diagnostic testing with molecular techniques and IHC. These additional testing results indicated that the majority of cases that were negative by the anti-ALK D5F3 IHC assay were also negative by another ALK IHC system, but were positive by one or more molecular assays. The slides from these cases were cut more than three months prior to staining, which may decrease sensitivity of the IHC assay.

There were 14 cases in this cohort that were uninformative by FISH (no result was obtained). Of these, three were evaluated as positive by both readers by the anti-ALK IHC assay. In addition, there were 19 cases where the FISH assay could not be performed, based on the H&E slide (usually due to the tumor content being insufficient). Of these, both readers evaluated the ALK IHC staining results as positive in four cases. Therefore, on average, 21% of the cases where FISH results were not obtained had a positive ALK status by the anti-ALK (D5F3) IHC assay.

The reproducibility of the ALK status as obtained by the anti-ALK IHC assay was determined. The ALK status obtained by each reader for the about 300 cases was compared. The results indicate that the anti-ALK IHC assay and scoring algorithm were highly reproducible between readers, as shown in Table 8.

TABLE 8

Scoring interpretation inter-reader precision

| Reader Comparison | | ALK Break Apart FISH | | |
|---|---|---|---|---|
| Reader 2 vs. Reader 1 | | Positive | Negative | Total |
| Anti-ALK D5F3 IHC | Positive | 56 | 0 | 56 |
| | Negative | 1 | 251 | 252 |
| | Total | 57 | 251 | 308 |

| Reader Comparison | | n/N | Percent | 95% Confidence Interval |
|---|---|---|---|---|
| Reader 2 vs. Reader 1 | Overall Percent Agreement | 307/308 | 99.7 | 98.2, 99.9 |
| | Average Positive Agreement | 112/113 | 99.1 | 97.0, 100.0 |
| | Average Negative Agreement | 502/503 | 99.8 | 99.4, 100.0 |

CONCLUSION

IHC with the anti-ALK (D5F3) Rabbit Monoclonal Primary Antibody was reproducible in its staining results for clinical ALK status on the BENCHMARK XT and BENCHMARK GX platforms. The binary scoring algorithm was highly reproducible across readers. The assay was concordant with the ALK break apart FISH method for ALK status.

Example 4

Effect of Tissue Processing Conditions on IHC Assay

This example describes the effect of varying tissue processing conditions on the IHC assay.

The H228 (ALK-positive) cell line was used to generate xenograft tumors in SCID mice. The tumors were harvested and fixed with different fixatives for varying times and were stained with the anti-ALK D5F3 antibody as described in Example 1.

Tissues fixed with 10% neutral buffered formalin for at least 6 hours yielded optimal ALK IHC staining results. Zinc formalin fixation for at least 6 hours also yielded acceptable ALK IHC staining. Fixation time of less than 6 hours in either neutral buffered formalin or zinc formalin resulted in significantly decreased staining intensity for ALK. Additional fixatives were also tested (AFA, B5, Prefer, and 95% ethanol) and resulted in significantly decreased ALK staining intensity at all time points.

Xenograft samples were harvested and left unfixed for times ranging from 30 minutes to 24 hours, then fixed for 12 hours in neutral buffered formalin. ALK staining intensity was decreased if the time to fixation was delayed more than 6 hours.

Sections that had been cut, but not stained, for various periods of time were also assessed for ALK IHC staining. ALK staining intensity decreased in sections that had been cut more than 3 months before staining and stored at room temperature. Despite decreased staining intensity, none of the ALK-positive cases changed status to ALK-negative.

Based on these data, fixation of samples within about 6 hours of collection in 10% neutral buffered formalin or zinc formalin for at least about 6 hours is recommended for optimal ALK staining results. In addition, staining is optimal if sections are stained within about 3 months of cutting, when stored at room temperature.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of identifying a subject as having non-small cell lung carcinoma (NSCLC) likely to respond to treatment with crizotinib, comprising:
   (a) contacting a sample comprising NSCLC tumor cells from the subject with an rabbit anti-ALK D5F3 antibody;
   (b) detecting ALK protein expression in the sample, comprising:
      (i) contacting the sample with a 3-hydroxyquinoxaline-2-carboxylic acid-conjugated secondary antibody which binds to the anti-ALK antibody;
      (ii) contacting the sample with a horseradish peroxidase-conjugated tertiary antibody which binds to the 3-hydroxyquinoxaline-2-carboxylic acid;
      (iii) contacting the sample with hydrogen peroxide and tyramide conjugated 3-hydroxyquinoxaline-2-carboxylic acid under conditions sufficient for deposition of the 3-hydroxyquinoxaline-2-carboxylic acid at or near the ALK protein; and
      (iv) contacting the sample with the tertiary antibody which binds to the 3-hydroxyquinoxaline-2-carboxylic acid
      (v) contacting the sample with hydrogen peroxide and 3,3'-diaminobenzidine tetrahydrochloride; and
      (vi) detecting the DAB precipitate utilizing light microscopy;
   (c) scoring the sample as positive or negative for ALK, comprising:
      (i) scoring the sample as positive for ALK if strong granular cytoplasmic staining is present in one or more tumor cells in the sample; or
      (ii) scoring the sample as negative for ALK if strong granular cytoplasmic staining is not present in one or more tumor cells in the sample; and
   (d) identifying the subject as having NSCLC likely to respond to treatment with crizotinib if the sample is scored as positive for ALK or identifying the subject as having NSCLC not likely to respond to treatment with crizotinib if the sample is scored as negative for ALK.

2. The method of claim 1, further comprising selecting the subject for treatment with crizotinib if the sample from the subject is scored as positive for ALK.

3. The method of claim 2, further comprising administering a therapeutically effective amount of crizotinib to the selected subject.

* * * * *